US007521242B2

(12) United States Patent
Court et al.

(10) Patent No.: US 7,521,242 B2
(45) Date of Patent: Apr. 21, 2009

(54) HOST CELLS DEFICIENT FOR MISMATCH REPAIR AND THEIR USE IN METHODS FOR INDUCING HOMOLOGOUS RECOMBINATION USING SINGLE-STRANDED NUCLEIC ACIDS

(75) Inventors: Donald L. Court, Frederick, MD (US); Xin-tian Li, Bejing (CN); Jian-Dong Huang, Hong Kong SAR (CN); Nina Costantino, Frederick, MD (US); Depei Liu, Beijing (CN)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 617 days.

(21) Appl. No.: 10/841,125

(22) Filed: May 7, 2004

(65) Prior Publication Data

US 2005/0079618 A1  Apr. 14, 2005

Related U.S. Application Data

(60) Provisional application No. 60/469,494, filed on May 9, 2003.

(51) Int. Cl.
*C12N 15/87* (2006.01)
*C12N 15/90* (2006.01)
*C12N 1/21* (2006.01)

(52) U.S. Cl. ................... 435/490; 435/471; 435/252.33
(58) Field of Classification Search ...................... None
See application file for complete search history.

(56) References Cited

U.S. PATENT DOCUMENTS

| 5,789,166 | A | 8/1998 | Bauer et al. |
| 5,888,732 | A | 3/1999 | Hartley et al. |
| 6,281,000 | B1 | 8/2001 | Chartier et al. |
| 6,355,412 | B1 | 3/2002 | Stewart et al. |
| 6,365,408 | B1 | 4/2002 | Stemmer |
| 6,509,156 | B1 | 1/2003 | Stewart et al. |
| 2002/0013956 | A1 | 1/2002 | Borts et al. |
| 2002/0151059 | A1 | 10/2002 | Te Riele et al. |
| 2005/0176149 | A1* | 8/2005 | Matic et al. ............... 435/488 |

FOREIGN PATENT DOCUMENTS

| WO | WO 95/22625 | 8/1995 |
| WO | WO 99/29837 | 6/1999 |
| WO | WO 01/04288 | 1/2001 |
| WO | WO 02/14495 | 2/2002 |
| WO | WO 02/062988 | 8/2002 |

OTHER PUBLICATIONS

Bilello et al., "Role of paracellular junction complexes in baculovirus-mediated gene transfer to nondiving rat hepatocytes," *Gene Therapy* 10:733-749, 2003.

Bubeck et al., "Rapid cloning by homologous recombination in vivo," *Nucl. Acid. Res.* 21: 3601-3602, 1993.
Capecchi, M., "Altering the Genome by Homologous Recombination," *Science* 244: 1288-1292, Jun. 1989.
Cho et al., "δ-Integration of endo/exo-glucanase and β-glucosidase genes into the yeast chromosomes for direct conversion of cellulose to ethanol," *Enzyme and Microbial Technology* 25: 23-30, Jul. 1999.
Copeland et al., "Recombineering: a powerful new tool for mouse functional genomics," *Nat. Rev. Genet.* 2: 769-779, 2001.
Court et al., "Genetic Engineering Using Homologous Recombination," *Annu. Rev. Genet.* 36: 361-388, 2002.
Cox, "Recombinational DNA Repair of Damaged Replication Forks in *Escherichia coli*," *Annu. Rev. Genet.*. 35: 53-82, 2001.
Degyrase et al., "In vivo intermolecular recombination in *Escherichia coli*: application to plasmid constructions," *Gene* 170: 45-50, 1996.
Ellis et al., "High efficiency mutagenesis, repair, and engineering of chromosomal DNA using single-stranded oligonucleotides," *Proc, Natl. Acad. Sci. USA* 98: 6742-6746, 2001.
Hall et al., "Homologous pairing and strand exchange promoted by the *Escherichia coli* RecT protein," *Proc. Natl. Acad. Sci.* 91: 3205-3209, 1994.
Harfe et al., "Mismatch repair proteins and mitotic genome stability," *Mut. Res.* 451: 151-167, 2000.
Higgins et al., "A Model for Replication Repair in Mammalian Cells," *J. Mol. Biol.* 101: 417-425, 1976.
Jasin et al., "Deletion of an Essential Gene in *Escherichia coli* by Site-Specific Recombination with Linear DNA Fragments," *J. Bacteriol.* 159: 783-9, 1984.
Karakousis et al., "The Beta Protein of Phage λ Binds Preferentially to an Intermediate in DNA Renaturation," *J. Mol. Biol.* 276: 721-731, 1998, abstract only.
Keim et al., "The RecE Recombination Pathway Mediates Recombination between Partially Homologous DNA Sequences: Structural Analysis of Recombination Products," *J. Struct. Biol.* 104: 97-106, 1990.
Kusano et al., "Involvement of RecE exonuclease and RecT annealing protein in DNA double-strand break repair by homologous recombination," *Gene* 138: 17-25, 1994.
Lee et al., "A highly efficient *Escherichia coli*-based chromosome engineering system adapted for recombinogenic targeting and subcloning of BAC DNA," *Genomics* 73: 56-65, 2001.
Li et al., "The Beta Protein of Phage λ Promotes Strand Exchange," *J. Mol. Biol.* 276: 733-744, 1998.
Maas et al., "Multicopy single-stranded DNA of *Escherichia coli* enhances mutation and recombination frequencies by titrating MutS protein," *Molec. Microbiol.* 19: (3) 505-509, 1996.

(Continued)

*Primary Examiner*—Nancy Vogel
(74) *Attorney, Agent, or Firm*—Klarquist Sparkman, LLP

(57) ABSTRACT

Methods are disclosed herein for inducing homologous recombination in a host cell comprising a target nucleic acid, using a single-stranded nucleic acid molecule. The single-stranded nucleic acid molecule has a sufficient number of nucleotides homologous to the target nucleic acid to enable homologous recombination with the target nucleic acid. The host cell includes a de-repressible promoter operably linked to a nucleic acid encoding a single-stranded binding protein and is deficient for mismatch repair. Isolated host cells of use in this method are also disclosed.

37 Claims, 3 Drawing Sheets

OTHER PUBLICATIONS

Moerschell et al., "Transformation of yeast with synthetic oligonucleotides," *Proc. Natl. Acad. Sci. U.S.A.* 85: 524-528, 1988.

Muniyappa et al., "The homologous recombination system of phage λ," *J. Bio. Chem.* 261: 7472-7478, Jun. 1986.

Murphy, K.C., "Use of bacteriophage λ recombination functions to promote gene replacement in *Escherichia coli*," *J. Bacteriol.* 180: 2063-2071, 1998.

Murphy et al., "PCR-mediated gene replacement in *Escherichia coli*," *Gene* 246: 321-330, 2000.

Muyrers, et al., "Point mutation of bacterial artificial chromosomes by ET recombination," *EMBO Rep.* 1: 239-243, 2000.

Muyrers et al., "RecE/RecT and Redα/Redβ initiate double-stranded break repair by specifically interacting with their respective partners," *Genes Dev.* 14: 1971-1982, 2000.

Muyrers et al., "Techniques: Recombinogenic engineering-new options for cloning and manipulating DNA," *Trends Biochem. Sci* 26: 325-331, 2001.

Muyrers et al., "Rapid modification of bacterial artificial chromosomes by ET-recombination," *Nucleic Acids Res.* 27: 1555-1557, 1999.

Nistala et al., "A reliable and efficient method for deleting operational sequences in PACs and BACs," *Uncle. Acid. Res.* 30: 10 e 41, 2002.

Nussbaum et al., "Restriction-Stimulated Homologous Recombination of Plasmids by the RecE Pathway of *Escherichia coli*," *Genetics* 130: 37-39, 1992.

Oliner et al., "In vivo cloning of PCR products in *E. coli*," *Nucl. Acids Res.* 21: 5192-5197, 1993.

Passy et al., "Rings and filaments of β protein from bacteriophage λ suggests a superfamily of recombination proteins," *Proc. Natl. Acad. Sci. U.S.A.* 96: 4279-4284, 1999.

Postow et al., "Topological challenges to DNA replication: Conformations at the fork," *Proc. Natl. Acad. Sci. USA* 98 (15): 8219-8226, 2001.

Poteete, "What makes the bacteriophage λ Red system useful for genetic engineering: molecular mechanism and biological function," *FEMS Microbiol. Lett.* 201: 9-14, 2001.

Reuven et al., "The Herpes Simplex Virus Type 1 Alkaline Nuclease and Single-Stranded DNA Binding Protein Mediate Strand Exchange In Vitro," *J. Virology* 77(13):7425-7433, 2003.

Santucci-Darmanin et al., "The DNA mismatch-repair MLH3 protein interacts with MSH4 in meiotic cells, supporting a role for this MutL homolog in mammalian meiotic recombination," *Hum. Mol. Genet.* 11: 1697-1706, 2002.

Smith, "Mechanism and Control of Homologous Recombination in *Escherichia coli*," *Ann Rev. Genet.* 21: 179-201, 1987.

Swaminathan et al., "Rapid Engineering of Bacterial Artificial Chromosomes Using Oligonucleotides," *Genesis* 29: 14-21, 2001.

Symington et al., "Intramolecular Recombination of Linear DNA Catalyzed by the *Escherichia coli RecE* Recombination System," *J. Mol. Biol.* 186: 515-525, 1985.

Vellani et al., "Bacteriophage SPP1 Chu Is an Alkaline Exonuclease in the SynExo Family of Viral Two-Component Recombinases," *J. Bacteriology* 185(8):2465-2474, 2003.

Yang et al., "Homologous recombination based modification in *Escherichia coli* and germline transmission in transgenic mice of bacterial artificial chromosome," *Nat. Biotechnol.* 15: 859-865, 1997.

Yu et al., "An efficient recombination system for chromosome engineering in *Escherichia coli*," *Proc. Natl. Acad. Sci. USA* 97: 5978-5983, 2000.

Zahrt et al., "Barriers to recombination between closely related bacteria: MutS and RecBCD inhibit recombination between *Salmonella typhimurium* and *Salmonella typhi*," *Proc. Natl. Acad. Sci. USA* 94:9786-9791, 1997.

Zhang et al., "A new logic for DNA engineering using recombination in *Escherichia coli*," *Nat. Genet.* 20: 123-128, 1998.

Zhang et al., "DNA cloning by homologous recombination in *Escherichia coli*," *Nat. Biotechnol.* 18: 1314-1317, 2000.

Costantino and Court "Enhanced Levels of λ Red-mediated recombinants in mismatch repair mutants," *PNAS*, 100(26) 15748-15753 (Dec. 23, 2003).

\* cited by examiner

HOST CELLS DEFICIENT FOR MISMATCH REPAIR AND THEIR USE IN METHODS FOR INDUCING HOMOLOGOUS RECOMBINATION USING SINGLE-STRANDED NUCLEIC ACIDS

CROSS-REFERENCE TO RELATED APPLICATIONS

This claims the benefit of U.S. Provisional Application No. 60/469,494, filed May 9, 2003, which is incorporated herein by reference. This also claims priority to International Patent Application No. PCT/US03/14657, filed May 9, 2003, which is also incorporated by reference herein.

FIELD

The present disclosure relates to methods to induce homologous recombination in cells in cells deficient for mismatch repair. It also relates to methods for modifying genomic DNA in bacterial artificial chromosomes (BACs) and to subcloning of genomic DNA from BACs into multi-copy plasmids. Cells of use for recombineering are disclosed that that are deficient for mismatch repair, and thus exhibit an increased frequency of homologous recombination.

BACKGROUND

Concerted use of restriction endonucleases and DNA ligases allows in vitro recombination of DNA sequences. The recombinant DNA generated by restriction and ligation may be amplified in an appropriate microorganism such as *E. coli*, and used for diverse purposes including gene therapy. However, the restriction-ligation approach has two practical limitations: first, DNA molecules can be precisely combined only if convenient restriction sites are available; second, because useful restriction sites often repeat in a long stretch of DNA, the size of DNA fragments that can be manipulated is limited, usually to less than about 25 kilobases.

Homologous recombination, generally defined as an exchange between homologous segments anywhere along a length of two DNA molecules, provides an alternative method for engineering DNA. In generating recombinant DNA with homologous recombination, a microorganism such as *E. coli*, or a eukaryotic cell such as a yeast or vertebrate cell, is transformed with exogenous DNA. The center of the exogenous DNA contains the desired transgene, whereas each flank contains a segment of homology with the cell's DNA. The exogenous DNA is introduced into the cell with standard techniques such as electroporation or calcium phosphate-mediated transfection, and recombines into the cell's DNA, for example with the assistance of recombination-promoting proteins in the cell.

A recombination system (termed "recombineering) has been developed for efficient chromosome engineering in *Escherichia coli* using electroporated linear DNA (see published PCT Application No. WO 02/14495 A2, which is herein incorporated by reference). A defective prophage supplies functions ($\lambda$ Red) that protect and recombine an electroporated DNA substrate in the bacterial cell. This system can be used with single-stranded DNA, as well as with linear double-stranded DNA (dsDNA). The use of recombination eliminates the requirement for standard cloning as all novel recombination sites are engineered by chemical synthesis in vitro, and the linear DNA is efficiently recombined in vivo. In this system, a temperature-dependent repressor tightly controls prophage expression, such that recombination functions can be transiently supplied by shifting cultures to 42° C. The efficient prophage recombination system does not require host RecA function and depends primarily on exo, bet, and gam functions expressed from the defective prophage. The defective prophage can be moved to other strains and can be easily removed from any strain. Importantly, recombination in this system is proficient with DNA homologies as short as 30-50 base pairs, making it possible to use PCR-amplified fragments as the targeting cassette. Gene disruptions and modifications of both the bacterial chromosome and bacterial plasmids are possible, and the system has been shown to be of use in the bacterial artificial chromosome libraries (see Published PCT Application No. WO 02/14495, herein incorporated by reference; Yu et al., *Proc. Natl. Acad. Sci. USA* 97:5978-5983, 2000).

This prophage system has been adapted for use in bacterial artificial chromosome (BAC) engineering by transferring it to DH10B cells, a BAC host strain. Fragments as large as 80 kb can be subcloned from BACs by gap repair using this recombination system, obviating the need for restriction enzymes or DNA ligases. BACs can be modified with this recombination system in the absence of drug selection (Lee et al., *Genomics* 73:56-65, 2001). It has been suggested that recombineering in BACs allows modification or subcloning of large fragments of genomic DNA with precision. This ability facilitates many kinds of genomic experiments that were difficult or impossible to perform previously and aid in studies of gene function. It has been suggested that this system is of use in generating mouse models and providing a refined analysis of the mouse genome (Copland et al., *Nat. Rev. Genet.* 2:769-779, 2001).

Recombineering uses the exo and bet functions of the prophage lambda under the control of a temperature sensitive repressor. When the lambda functions are turned on, cells become more "recombinogenic," that is they take up DNA and recombination of the DNA occurs with a target sequence in the cell. This system has been adapted for use in bacterial artificial chromosome engineering, wherein inducible recombinases (e.g. cre or flpe) are introduced into host cells and BAC modification is accomplished using recombination sites (e.g. loxP or frt, respectively). This system can be used to generate Cre-expressing transgenic mice for use in conditional knock-out studies. This system utilizes a targeting vector to introduce recombination sites (e.g. loxP) into a gene of interest. Expression of a recombinase from a specific promoter (such that expression occurs in a tissue of interest) results in recombination at the recombination sites, leading to a "conditional knock-out."

It has also been shown that synthetic single-stranded oligonucleotides (SSOs) can also be used in place of linear dsDNA fragments, to create sequence-specific mutations (Ellis et al., *Proc. Natl Acad Sci USA* 98:6742-6746, 2001; Swaminathan et al., *Genesis* 29:14-21, 2001). However, the mechanism(s) by which SSOs affect these genetic changes remains to be established. In addition, although recombineering using SSOs provides a method for introducing homologous DNA into a target nucleic acid sequence, the frequency of recombination can be improved. Thus, methods for increasing recombination frequency using recombineering, and strains which produce recombinants at a high frequency are disclosed herein.

SUMMARY

This disclosure provides methods for inducing homologous recombination using single-stranded or double-stranded oligonucleotides in host cells. Host cells are of use in increasing the efficiency of recombination using the bet (and optionally exo and gam) functions of the prophage lambda under the control of a de-repressible promoter, and are deficient for mismatch repair. In one specific, non-limiting example the promoter is lambda PL promoter, which is under the control of a temperature sensitive repressor. In one specific, non-limiting example, the nucleic acid nucleic acid is single-stranded.

The host cells of use in these methods are deficient for mismatch repair. Thus, in one embodiment, the host cell is a bacterial cell that is deficient for mismatch repair. Specific, non-limiting examples are bacterial cells that have reduced or absent function of the polypeptides encoded by mutS, mutH, mutL, uvrD, and/or or dam, such that the bacterial cell is deficient for mismatch repair.

The methods include introducing a single-stranded or double-stranded homologous nucleic acid of sufficient homology to a target sequence into a host cell deficient for mismatch repair. The homologous nucleic acid is of sufficient length to undergo homologous recombination with the target sequence, and can optionally include a mutation as compared to the target sequence. The host cell includes a de-repressible promoter operably linked to a nucleic acid encoding Beta. Activation of the de-repressible promoter, such that the expression of Beta is induced, results in recombination of the homologous nucleic acid with the target nucleic acid. In additional embodiments, the de-repressible promoter is also operably linked to a nucleic acid encoding Exo and or Gam. In further embodiments, the host cell is a bacterial cell, a yeast cell, or a mammalian cell.

The foregoing and other features and advantages will become more apparent from the following detailed description of several embodiments, which proceeds with reference to the accompanying figures.

SEQUENCE LISTING

Figure 1:
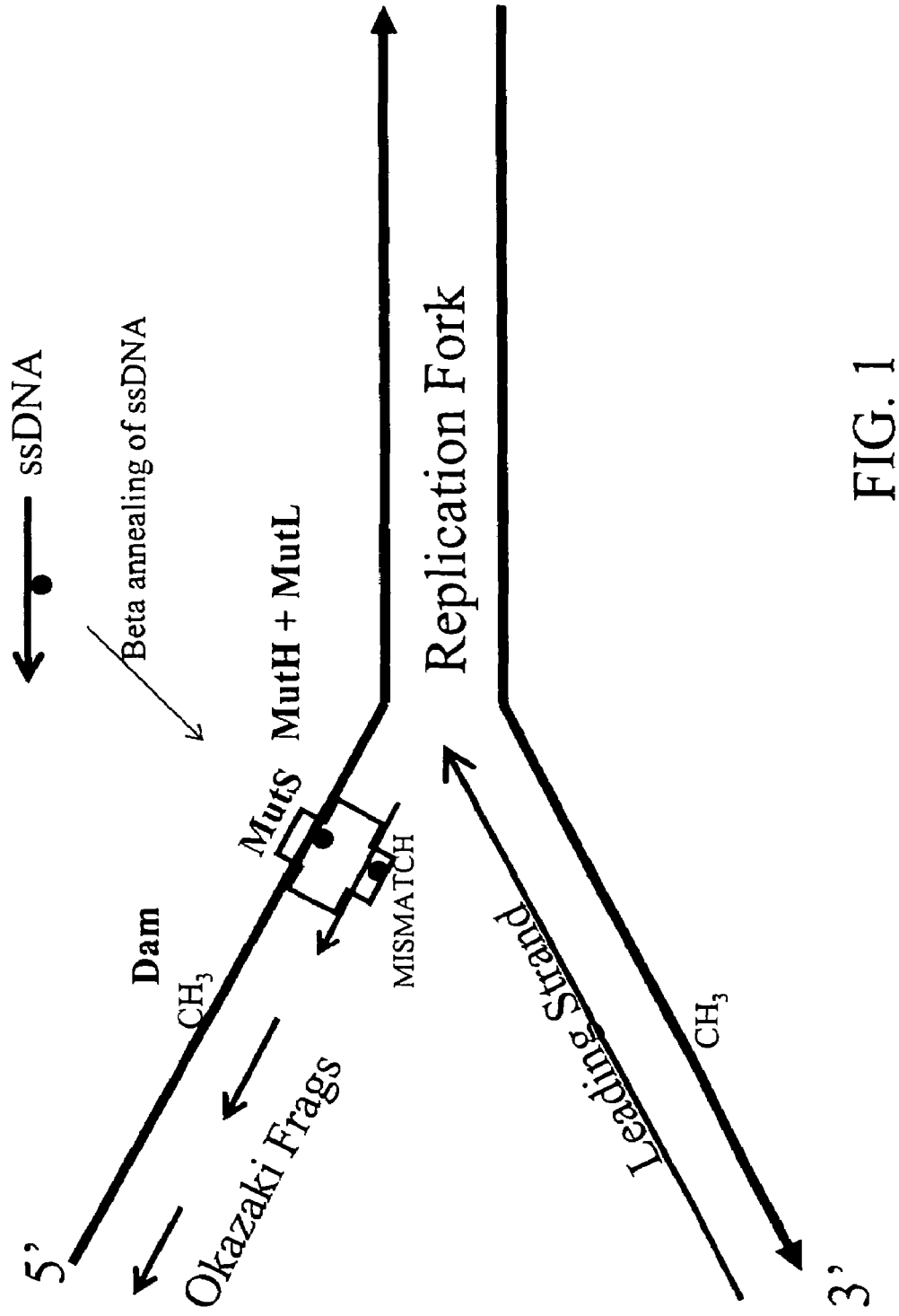
FIG. 1 is a schematic diagram of single stranded DNA at the replication fork. Both the leading and the lagging strand are shown. A single stranded nucleic acid is utilized for recombination that includes a mismatch. The annealing of the single-stranded nucleic acid, mediated by Beta, is indicated on the replication fork. MutS, MutH, MutL, and dam are shown at the replication fork. If present, these proteins will correct the mismatch. A strain that is deficient for MutS, MutH, MutL, dam (or uvrD) will not repair the mismatch, and thus an increased recombination frequency will be detected.

The nucleic and amino acid sequences listed in the accompanying sequence listing are shown using standard letter abbreviations for nucleotide bases, and three letter code for amino acids, as defined in 37 C.F.R. 1.822. For double-stranded nucleic acids, only one strand of each nucleic acid sequence is shown, but the complementary strand is understood as included by any reference to the displayed strand. However, for single-stranded nucleic acids, the complementary strand is not included.

DETAILED DESCRIPTION

I. Abbreviations
  Amp: ampicillin
  BAC: bacterial artificial chromosome
  ddH$_2$O: double distilled water
  DNA: deoxyribonucleic acid
  ds: double-stranded
  IPTG: isopropyl-beta-D-thiogalactopyranoside
  Kan: kanamycin
  Lag: lagging
  Lead: leading
  ml: milliliter
  min: minute(s)
  MMR: mismatch repair
  ng: nanograms
  nt: nucleotide
  NT oligo: non-template oligonucleotide
  Oligo: oligonucleotide
  PCR: polymerase chain reaction
  ss: single-stranded
  SSO or ss oligo: single-stranded oligonucleotide
  T oligo: template oligo
  µl: microliter
  YAC: yeast artificial chromosome II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

3' overhang: Two nucleic acid sequences which when annealed are partially double-stranded and partially single-stranded. The single-stranded end or ends extend away from the double-stranded segment in a 5' to 3' direction.

5' overhang: Two nucleic acid sequences which when annealed are partially double-stranded and partially single-stranded. The single-stranded end or ends extend away from the double-stranded segment in a 3' to 5' direction.

Bacterial artificial chromosome (BAC): Bacterial artificial chromosomes (BACs) have been constructed to allow the cloning of large DNA fragments in *E. coli*, as described in O'Conner et al., *Science* 244:1307-1312, 1989; Shizuya et al., *Proc. Natl. Acad. Sci. USA* 89:8794-8797, 1992; Hosoda et al., *Nucleic Acids Res.* 18:3863-3869, 1990; and *Current Protocols in Molecular Biology*, ed. Ausubel et al., Greene Publishing and Wiley-Interscience, New York, 1987 (with periodic updates). This system is capable of stably propagating mammalian DNA over 300 kb. In one embodiment, a BAC carries the F replication and partitioning systems that ensure low copy number and faithful segregation of plasmid DNA to daughter cells. Large genomic fragments can be cloned into F-type plasmids, making them of use in constructing genomic libraries.

Beta: The 28 kDa lambda Beta ssDNA binding polypeptide (and nucleic acid encoding lambda Beta) involved in double-strand break repair homologous recombination. DNA encoding Beta (bet) and polypeptide chains having lambda Beta activity are also referred to herein as bet (see published PCT Application No. WO 02/14495 A2, herein incorporated by reference). The lambda Beta protein binds to single-stranded DNA and promotes renaturation of complementary single-strand regions of DNA (see Karakousis et al, *J. Mol. Biol.* 276:721-733, 1998; Li et al., *J. Mol. Biol.* 276:721-733, 1998; Passy et al., *PNAS* 96:4279-4284, 1999).

Functional fragments and variants of Beta include those variants that maintain their ability to bind to ssDNA and mediate the recombination function of lambda Beta as described herein, and in the publications referenced herein. It is recognized that the gene encoding Beta may be considerably mutated without materially altering the ssDNA binding function or homologous recombination function of lambda Beta. First, the genetic code is well-known to be degenerate, and thus different codons encode the same amino acids. Second, even where an amino acid mutation is introduced, the mutation may be conservative and have no material impact on the essential functions of lambda Beta. See Stryer, Biochemistry 3rd Ed., (c) 1988. Third, part of the lambda Beta polypeptide chain may be deleted without impairing or eliminating its ssDNA binding protein function, or its recombination function. Fourth, insertions or additions may be made in the lambda Beta polypeptide chain—for example, adding epitope tags—without impairing or eliminating its essential functions (*Current Protocols in Molecular Biology*, ed. Ausubel et al., Greene Publishing and Wiley-Interscience, New York, 1987 (with periodic updates)).

Biolistics: Insertion of DNA into cells using DNA-coated micro-projectiles. Also known as particle bombardment or microparticle bombardment. The approach is further described and defined in U.S. Pat. No. 4,945,050.

cDNA (complementary DNA): A piece of DNA lacking internal, non-coding segments (introns) and regulatory sequences that determine transcription. cDNA may be synthesized in the laboratory by reverse transcription from messenger RNA extracted from cells.

Cosmid: Artificially constructed cloning vector containing the cos gene of phage lambda. Cosmids can be packaged in lambda phage particles for infection into *E. coli*; this permits cloning of larger DNA fragments (up to 45 kb) than can be introduced into bacterial hosts in plasmid vectors.

De-repressible Promoter: When a repressor is bound to a de-repressible promoter transcription is substantially decreased as compared to transcription from the de-repressible promoter in the absence of repressor. By regulating the binding of the repressor, such as by changing the environment, the repressor is released from the de-repressible promoter, and transcription increases. In this definition, a de-repressible promoter does not require an activator for transcription. One specific, non-limiting example is the PL promoter, which is regulated by the repressor cI, but is not activated by an activator. (The arabinose promoter is not a simple de-repressible promoter as arabinose inactivates the repressor AraC and converts it to an activator).

In one embodiment, the de-repressible promoter is a temperature sensitive de-repressible promoter. For example, by increasing the temperature, the repressor is released from the promoter, or can no longer bind to the promoter with a high affinity, and transcription is increased from the promoter. One specific, non-limiting example is the induction of PL promoter activity by increasing the temperature of the cell. Increased temperature inactivates a temperature-sensitive repressor cI, allowing genes that are operably linked to the PL promoter to be expressed at increased levels. One of skill in the art can readily identify a de-repressible promoter.

In one embodiment, a de-repressible promoter is auto-regulated. For example, if only one copy of a gene encoding cI is present, yet many copies of the PL promoter are present, expression of cI is upregulated such that transcription is blocked from any of the PL promoters.

Double-strand break repair recombination: A type of homologous recombination exemplified by the lambda recombination proteins Exo, Beta and Gam, and shared by numerous other recombinase systems. A double-strand break is the initiation point for concerted action of recombination proteins. Typically, an exonuclease degrades processively from the 5' ends of these break sites, and ssDNA binding polypeptide binds to the remaining 3' single-strand tail, protecting and preparing the recessed DNA for homologous strand invasion (Szostak et al., *Cell* 33:25-35, 1983; Little, *J. Biol. Chem.* 242:679-686, 1967; Carter et al., *J. Biol. Chem.* 246:2502-2512, 1971; Lindahl et al., *Science* 286:1897-1905, 1999). Examples of ssDNA binding polypeptides which bind to either ssDNA and/or dsDNA with 3' overhangs and promote double-strand break repair recombination include lambda Beta, RecT of *E. coli*, Erf of phage p22, and Rad52 in various eukaryotic cells including yeast and mammalian cells.

Electrocompetent: Cells capable of macromolecular uptake upon treatment with electroporation.

Electroporation: A method of inducing or allowing a cell to take up macromolecules by applying electric fields to reversibly permeabilize the cell walls. Various methods and apparatuses used are further defined and described in: U.S. Pat. Nos. 4,695,547; 4,764,473; 4,946,793; 4,906,576; 4,923,814; and 4,849,089.

Eukaryotic cell: A cell having an organized nucleus bounded by a nuclear membrane. These include lower organisms such as yeasts, slime molds, and the like, as well as cells from multicellular organisms such as invertebrates, vertebrates, and mammals. They include a variety of tissue types, such as: endothelial cell, smooth muscle cell, epithelial cell, hepatocyte, cells of neural crest origin, tumor cell, hematopoietic cell, immunologic cell, T cell, B cell, monocyte, macrophage, dendritic cell, fibroblast, keratinocyte, neuronal cell, glial cell, adipocyte, myoblast, myocyte, chondroblast, chondrocyte, osteoblast, osteocyte, osteoclast, secretory cell, endocrine cell, oocyte, and spermatocyte. These cell types are described in standard histology texts, such as McCormack, *Introduction to Histology*, (c) 1984 by J. P. Lippincott Co.; Wheater et al., eds., *Functional Histology*, 2nd Ed., (c) 1987 by Churchill Livingstone; Fawcett et al., eds., Bloom and Fawcett: *A Textbook of Histology*, (c) 1984 by William and Wilkins.

Exo: The exonuclease of lambda (and the nucleic acid encoding the exonuclease protein) involved in double-strand break repair homologous recombination. See published PCT Application No. WO 02/14495 A2 and references therein for discussion.

Gam: A lambda protein (and nucleic acid encoding Gam) involved in double-strand break repair homologous recombination. It is believed to inhibit cellular nuclease activity such as that encoded by the recBCD and sbcC system of *E. coli*. See published PCT Application No. WO 02/14495 A2 for discussion. Over-expression of Gam function, when expressed in the cell, is extremely toxic to the cell, and prevents growth. For this reason tight controls over its expression are always required. PL and cI 857 are able to regulate Gam expression.

Functional fragments and variants of Exo and Gam: As discussed for Beta (see "Functional Fragments And Variants Of Beta"), it is recognized that genes encoding Exo or Gam may be considerably mutated without materially altering their function, because of genetic code degeneracy, conservative amino acid substitutions, noncritical deletions or insertions, etc. Unless the context makes it otherwise clear, the term lambda Exo, Exo, or lambda exonuclease are all intended to include the native lambda exonuclease, and all fragments and variants of lambda exonuclease.

Extrachromosomal: Not incorporated into the chromosome or chromosomes of a cell. In the context of nucleic acids, extrachromosomal indicates a DNA oligonucleotide that is not covalently incorporated into the chromosome or chromosomes of a cell. Intrachromosomal refers to material such as an oligonucleotide that is incorporated into the chromosome or chromosomes of a cell, such as a DNA oligonucleotide covalently incorporated into the chromosomal DNA of a cell.

Homologous arm: Nucleotides at or near 5' or 3' end of a polynucleotide which are identical or similar in sequence to the target nucleic acid in a cell, and capable of mediating homologous recombination with the target nucleic acid. Homologous arms are also referred to as homology arms. In one embodiment, a homology arm includes at least 20 bases of a sequence homologous to a nucleic acid of interest. In another embodiment, the homology arm includes at least 30 base pairs of a sequence homologous to a nucleic acid of interest. In yet another embodiment, a homology arm includes at least 40 base pairs of a sequence homologous to a nucleic acid of interest. In a further embodiment, a homology arm includes from about 50 to about 100 base pairs of a sequence homologous to a nucleic acid of interest.

Homologous recombination: An exchange of homologous polynucleotide segments anywhere along a length of two nucleic acid molecules. Homologous nucleic acids include nucleic acids that are 100% identical, as well as nucleic acids with limited differences in their nucleic acid sequence. For example, homologous recombination can occur between two nucleic acid sequences that are at least 90% identical, such as nucleic acid sequences that are at least 91%, at least 92%, at least 93%, at least 94%, at least 95%, at least 96%, at least 97%, at least 98%, or at least 99%, identical.

Host cell: A cell that is used in laboratory techniques such as DNA cloning to receive exogenous nucleic acid molecules. In one embodiment, a host cell is used to maintain or allow the reproduction of a vector, or to facilitate the manipulation of nucleic acid molecules in vitro. A host cell can be a prokaryotic or a eukaryotic cell. In one embodiment, a host cell is a bacterial cell, such as, but not limited to, an E. coli cell (e.g. DH10B, DY330, HME6, HME41, or DY380).

HVJ-mediated gene transfer: A method of macromolecular transfer into cells using inactivated hemagglutinating virus of Japan and liposomes, as described in Morishita et al., J. Clin. Invest. 91:2580-2585, 1993; Morishita et al., J. Clin. Invest. 94:978-984, 1994.

Inducible promoter: A promoter whose activity may be increased by some change in the environment of the cell. Examples of inducible promoters abound in nature, and a broad range of environmental or hormonal changes may activate or repress them. One specific, non-limiting example of an inducible promoter is the arabinose promoter.

Isolated: An "isolated" biological component (such as a nucleic acid or protein) has been substantially separated or purified away from other biological components in the cell of the organism in which the component naturally occurs, i.e., other chromosomal and extra-chromosomal DNA and RNA, and proteins. Thus, nucleic acids and proteins that have been "isolated" include nucleic acids and proteins purified by standard purification methods. The term also embraces nucleic acids and proteins prepared by recombinant expression in a host cell as well as chemically synthesized nucleic acids.

Lagging and Leading Strand of a double-stranded (ds) DNA: The leading strand is the strand of a double-stranded DNA that is synthesized continuously during replication. The lagging strand is the strand of a double-stranded DNA that is synthesized discontinuously.

Okazaki fragments are short segments of newly synthesized DNA produced during replication. All the known DNA polymerases only synthesize DNA in one direction, the 5' to 3' direction. However, as the strands separate, the replication fork moves along one parental strand in the 3' to 5' direction and 5' to 3' on the other parental strand. On the former, the leading strand, DNA is synthesized continuously in the 5' to 3' direction. On the other, the lagging strand, DNA synthesis only occurs when a length of single-stranded (ss) DNA has been exposed and proceeds in the direction opposite to the movement of the replication fork (5' to 3). Thus, it is discontinuous, and the series of fragments are polymerized and then covalently linked by ligases to give a continuous strand. In eukaryotes, Okazaki fragments are typically a few hundred nucleotides in length, whereas in prokaryotes they can be several thousand nucleotides in length.

Linear plasmid vector: A DNA sequence (1) containing a bacterial plasmid origin of replication, (2) having a free 5' and 3' end, and (3) capable of circularizing and replicating as a bacterial plasmid by joining its free 5' and 3' ends. Examples of linear plasmid vectors include the linearized pBluescript vector and linearized pBR322 vectors.

Lipofection: The process of macromolecular transfer into cells using liposomes. See U.S. Pat. No. 5,651,981.

Mini lambda: A derivative of lambda (λ) wherein most of the viral lytic genes, including those required for replication and lysis, are deleted. A mini-lambda maintains the Red functions (Beta, with, or without, Exo and/or Gam) for homologous recombination and maintains the integration/excision functions (e.g. att, integrase (int). and excisionase (xis)) to insert and excise its DNA from the chromosome.

Mismatch: A base-pair in a double-stranded nucleic acid that does not mate via normal Watson-Crick binding (e.g., G/C, A/T. For example, in the structure diagrammed below:

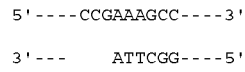

There is a base pair mismatch at the 3' end of the lower strand. Base pair mismatches include any homologous pairing of nucleotides (A/A, T/T, G/G, and C/C), as well as some heterologous pairings (G/A, G/T, C/A, C/G) of nucleotides. Mismatch is also a small insertion/deletion loop in double-stranded DNA. Thus, in a structure such as

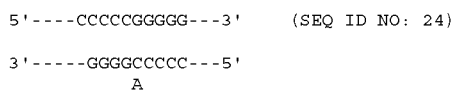

the A represents a base inserted into the bottom stand that is a "mismatch" as there is no corresponding base with which it forms Watson-Crick base pairs within the upper strand.

Although the examples shown are based on a single nucleotide difference, the mismatch can be for a longer length of nucleic acid, such as but not limited to, a mismatch of about one, two, three, four, five, or ten nucleotides.

Mismatch Repair and Polypeptides Involved in Mismatch Repair: The endogenous pathway in cells response for the repair of a mismatch. In prokaryotes (e.g., *E. coli*), the MutS, MutL, MutH, dam, and uvrD proteins are involved in mismatch repair, amongst others.

Briefly, in a bacterial cell, the MutS protein recognizes and binds to mismatches in DNA duplexes. Briefly, a mismatch existing in the form of a base-base mispair of a small insertion/deletion loop in double-stranded DNA is bound by a MutS protein homodimer (e.g., see Genbank Accession No. NP_417213). Multiple MutS homodimers can bind to form a multimer complex until a hemimethylated GATC site is encountered. The MutL (e.g. see GenBank Accession No. NP_418591) protein binds to MutS, and the MutH protein (e.g. see GenBank Accession No. NP_417308) binds to hemimethylated dam methylation sites (which are methylated by dam, see, for example, GenBank Accession No. NP_417846). The MutS-MutL-DNA complex stimulates MutH to cleave the unmethylated DNA strand at the GATC sequence (the GATC site can be either 5' or 3' of the recognized mismatch). One of two exonucleases (depending on whether cleavage was 5' or 3') chews away at the DNA to beyond the mismatch site, such that long patch repair synthesis can occur. Excision is accomplished by cooperation between the uvrD (helicase II, e.g. see GenBank Accession No. NP_418258) protein, which unwinds from the nick in the direction of the mismatch, and a single-strand specific exonuclease of appropriate polarity, followed by resynthesis (polymerase III) and ligation (DNA ligase). For a review of mismatch repair pathways, see Marti et al., *J. Cell. Physiol.* 191:28-41, 2002.

Eurkaryotes have proteins with sequence similarity to MutS and MutL that are involved in a similar repair pathway. The eucaryotic MutS is a dimer of MSH2 and GTBP (now known as MSH3 or MSH6) proteins. Eucaryotic MutL also consists of two polypeptides, MLH1 and PMS2. One of skill in the art can readily identify the eurkaryotic proteins involved in mismatch repair. In addition, a table (Table 2) describing exemplary proteins is provided in the disclosure herein.

Nucleic acid: A deoxyribonucleotide or ribonucleotide polymer in either single or double-stranded form, including known analogs of natural nucleotides unless otherwise indicated.

Oligonucleotide: A single-stranded nucleic acid ranging in length from 2 to about 500 bases, for example, polynucleotides that contain at least 20 or 40 nucleotides. Oligonucleotides are often synthetic but can also be produced from naturally occurring polynucleotides.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Phagemid artificial chromosome: Also referred to as P1 artificial chromosome. A type of artificial chromosome allowing for stable cloning of very large DNA fragments. Further described in Shepherd et al., *Proc. Natl. Acad. Sci. USA* 92:2629, 1994; Iannou et al., *Nature Genetics* 6:84-89, 1994.

Phage-based recombination systems: Bacteria such as *E. coli* encode their own homologous recombination systems, which are used in repair of DNA damage and to maintain a functional chromosome. The viruses or phages that inhabit bacteria often carry their own recombination functions. Phage λ carries the Red recombination system. These phage systems can work with the bacterial recombination functions or independently of them.

PL promoter: The major leftward promoter of bacteriophage lambda. Once the lambda DNA is incorporated into the bacterial chromosome, transcription from this promoter is tightly repressed by the cI repressor. Upon inactivation of the cI repressor, for example by heat shock of a temperature sensitive mutant, transcription from the PL promoter is activated, leading to expression of lambda genes. See Sambrook et al., Cold Spring Harbor Laboratory Press, Cold Spring Harbor, N.Y., 1989, and Oppenheim et al., *Prog. Nucleic Acid Res. Mol. Biol.* 46:37-49, 1993.

Plasmid: Autonomously replicating, extrachromosomal DNA molecules, distinct from the normal bacterial genome and nonessential for bacterial cell survival under nonselective conditions.

Polynucleotide: A double-stranded or single-stranded nucleic acid sequence of any length. Therefore, a polynucleotide includes molecules which are 15, 50, 100, 200 nucleotides long (oligonucleotides) and also nucleotides as long as a full length cDNA.

Polypeptide: Any chain of amino acids, regardless of length or post-translational modification (e.g., glycosylation or phosphorylation).

Prokaryote: Cell or organism lacking a membrane-bound, structurally discrete nucleus and other subcellular compartments. Prokaryotes include Archaea, and Bacteria. Bacterial include hydrogenobacteria, Thermotogales, green non-sulfur bacteria, the deioncoccus group, Cyanobacteria, plancotmyces, spirochetes, spirilla, myxobacteria, lithotrophs, pseudomonads, enteric bacteria, vibrios, green sulfur bacteria, cytophagas, pyogenic cocci, and Gram Positive bacteria. Thus, prokaryotes include both gram positive and gram negative bacteria (e.g. *Staphylococcus aureus*, *Streptococcus pyogenes*, and *Streptococcus pneumonia*). In one specific, non-limiting example a prokaryote is a bacteria, such as a gram-negative bacteria, such as an enteric bacteria (e.g., *E. coli*).

Probes and primers: A nucleic acid probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al., Cold Spring Harbor Laboratory Press, Cold Spring Harbor, N.Y., 1989, and *Current Protocols in Molecular Biology*, ed. Ausubel et al., Greene Publishing and Wiley-Interscience, New York, 1987 (with periodic updates).

Primers are short nucleic acids, preferably DNA oligonucleotides 15 nucleotides or more in length. Primers may be annealed to a complementary target DNA strand by nucleic acid hybridization to form a hybrid between the primer and the target DNA strand. The 3' hydroxyl end of the primer may be then extended along the target DNA strand through the use of a DNA polymerase enzyme. Primer pairs (one on either side of the target nucleic acid sequence) can be used for amplification of a nucleic acid sequence, e.g., by the polymerase chain reaction (PCR) or other nucleic-acid amplification methods known in the art.

Methods for preparing and using probes and primers are described, for example, in Sambrook et al., Cold Spring Harbor Laboratory Press, Cold Spring Harbor, N.Y., 1989, Ausubel et al., supra (1987). PCR primer pairs can be derived from a known sequence, for example, by using computer programs intended for that purpose such as Primer (Version 0.5, © 1991, Whitehead Institute for Biomedical Research, Cambridge, Mass.). Under appropriate conditions, the specificity of a particular probe or primer increases with its length. Thus, in order to obtain greater specificity, probes and primers may be selected that comprise 20, 25, 30, 35, 40, 50 or more consecutive nucleotides of related cDNA or gene sequence.

Purified: The term purified does not require absolute purity; rather, it is intended as a relative term. Thus, for example, a purified lambda Beta preparation or ssDNA binding polypeptide is one in which the protein is more enriched than the protein is in its natural environment within a cell. Preferably, a preparation of lambda Beta is purified such that the polypeptide represents at least 50% of the total protein content of the preparation.

RecA: The RecA protein is a central protein that has an activity as in the recombination function of *E. coli*. Homologues are found in all other organisms. RecA protein allows two homologous DNAs to find each other among non-homologous DNAs and then trade or transfer strands with each other. This exchange occurs by RecA binding to a single-stranded region in one of the DNAs and using that strand to search for its dsDNA homolog, binding to the dsDNA and causing the single-strand to pair with its complement in the dsDNA ultimately displacing the identical strand of the duplex. This strand transfer generates a key intermediate in theRecA-mediated recombination process.

recE recT genes and the Rac prophage: *E. coli* and other bacteria contain in their chromosomes remnants of viruses. These viruses or prophages are for the most part defective and may contain only a few genes of the original virus. In *E. coli*, one defective prophage is called Rac. Two genes, recE and recT of the Rac prophage, encode homologous recombination functions. These genes are normally silent but the sbcA mutation activates their constitutive expression. Thus, the sbcA mutant is active for recombination.

Recombinases: Proteins that, when included with an exogenous targeting polynucleotide, provide a measurable increase in the recombination frequency between two or more oligonucleotides that are at least partially homologous.

Recombineering: The use of a recombinase to mediate homologous recombination between linear DNA introduced into a living cell and a replicon in the cell. The linear DNA can be either single or double stranded. A recombineering system is described in published PCT Application No. WO 02/14495 A2, which is herein incorporated by reference. In one embodiment, recombineering uses the bet functions (and optionally exo and gam) of the prophage lambda under the control of a de-repressible promoter, such as but not limited to, a promoter regulated by a temperature sensitive repressor. When the lambda functions are turned on, cells become more "recombinogenic," that is they take up DNA and recombination of the DNA occurs with a target sequence in the cell. This system has been adapted for use in bacterial artificial chromosome engineering, and can also be used with yeast artificial chromosomes. Recombineering can be modified to use other functions, such as, but not limited to 34.1 gene from *Bacillus subtilis* phage SPP1, which encodes the polypeptide Chu (the product of 34.1) or herpes simplex virus (HSV) UL29 (Vellani and Meyers, *J. Bacteriol.* 185: 2465-74, 2003). Recombineering can be used to introduce mutations into a target sequence in both eukaryotic and prokaryotic cells.

Selection markers or selectable markers: Nucleic acid sequences which upon intracellular expression are capable of being detected, such a nucleic acid sequence that confers either a positive or negative selection marker or phenotypic characteristic for the cell expressing the sequence. The term "selection marker" or "selectable marker" includes both positive and negative selection markers. A "positive selection marker" is a nucleic acid sequence that allows the survival of cells containing the positive selection marker under growth conditions that kill or prevent growth of cells lacking the marker. Examples of a positive selection marker is a nucleic acid sequence which promotes expression of the neomycin resistance gene, ampicillin resistance gene, and kanamycin resistance gene. Cells not containing the neomycin resistance gene are selected against by application of G418, whereas cells expressing the neomycin resistance gene are not harmed by G418 (positive selection). A "negative selection marker" is a nucleic acid sequence that kills, prevents growth of or otherwise selects against cells containing the negative selection marker, usually upon application of an appropriate exogenous agent. An example of a negative selection marker is the sacB gene, which encodes a function causing sensitivity to the addition of sucrose to the culture. Another example of a negative marker is a nucleic acid sequence which promotes expression of the thymidine kinase gene of herpes simplex virus (HSV-TK). Cells expressing HSV-TK are selected against by application of ganciclovir (negative selection), whereas cells not expressing the gene are relatively unharmed by ganciclovir. The terms are further defined, and methods further explained, by U.S. Pat. No. 5,464,764.

Sequence identity: The similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar are the two sequences.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Bio.* 48:443, 1970; Pearson and Lipman, *Methods in Molec. Biology* 24:307-331, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang et al., *Computer Applications in BioSciences* 8:155-165, 1992; and Pearson et al., *Methods in Molecular Biology* 24:307-331,1994. Altschul et al. (1994) presents a detailed consideration of sequence alignment methods and homology calculations.

The NCBI Basic Local Alignment Search Tool (BLAST) (Altschul et al., *J. Mol. Biol.* 215:403-410, 1990) is available from several sources, including the National Center for Biological Information (NBCI, Bethesda, Md.) and on the Internet, for use in connection with the sequence analysis programs blastp, blastn, blastx, tblastn and tblastx. It can be accessed at the NCBI website, together with a description of how to determine sequence identity using this program.

Homologues of lambda Beta, Exo and Gam, and ssDNA binding proteins typically possess at least 60% sequence identity counted over full-length alignment with the amino acid sequence of the protein being evaluated (that is, lambda Beta, Exo or Gam, or ssDNA binding protein such as P22 Erf, RecT, and Rad52) using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 95%, at least 98%, or at least 99% sequence identity. When less than the entire sequence is being compared for sequence identity, homologs will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI website.

Similarly the identity between a target nucleic acid sequence and a homologous single-stranded nucleic acid sequence using the NCBI Basic Local Alignment Search Tool (BLAST) (Altschul et al., *J. Mol. Biol.* 215:403-410, 1990), as available from several sources, including the National Center for Biological Information (NBCI, Bethesda, Md.) and on the Internet. It can be accessed at the NCBI website, together with a description of how to determine sequence identity of nucleotide sequences.

One of skill in the art will appreciate that these sequence identity ranges are provided for guidance only; sequences of sufficient identity to provide homologous recombination activity could be obtained that fall outside of the ranges provided.

Single-stranded DNA (ssDNA) and double-stranded DNA (dsDNA): ssDNA is DNA in a single polynucleotide chain; the DNA bases are not involved in Watson-Crick base pairing with another polynucleotide chain. dsDNA involves two or more complementary polynucleotide chains, in which the two polynucleotide chains are at least partially Watson-Crick base-paired to each other. Double-stranded DNA can also include a segment of DNA that is partially ssDNA and partially dsDNA, for example if there are gaps in one polynucleotide chain of a segment of dsDNA, such as a DNA including 5' or 3' overhangs. ssDNA and dsDNA may contain nucleotide analogs, nonnaturally occurring or synthetic nucleotides, biotin, or epitope or fluorescent tags. ssDNA or dsDNA may be labeled; typical labels include radioactive isotopes, ligands, chemiluminescent agents, and enzymes.

Site-specific recombinase: A recombinase whose activity is limited to DNA of a specific sequence. Examples include the Cre, FLP and FLPE recombinases. Lambda Int is specific for its att site. Cre recombinases are site-specific for loxp recombination sites in a DNA sequence, whereas FLP and FLPE recombinases are site-specific for FRT recombination sites. A recombination site is a nucleic acid sequence specifically recognized by a recombinase. For example, the Cre recombinase specifically binds a loxp recombination site, and thereby induces recombination.

Substantially purified: A polynucleotide or polypeptide which is substantially free of other nucleotides, proteins, lipids, carbohydrates or other materials with which it is naturally associated. For example, a polypeptide may be at least 50%, 80% or 90% free of other proteins, lipids, carbohydrates or other materials with which it is naturally associated. In another example, a polynucleotide may be isolated from the nucleotide sequences found 5' and 3' from the sequence in a wild-type cell.

Target nucleic acid sequence: The nucleic acid segment which is targeted for homologous recombination. Typically, this is a segment of chromosomal or extrachromosomal DNA in a cell. Extrachromosomal DNA harboring target nucleic acid sequences may include episomal DNA, plasmid DNA, bacterial artificial chromosome, phagemid artificial chromosomes, yeast artificial chromosomes, cosmids, and the like. In one embodiment, the target nucleic acid sequence harbors a gene or gene fragment which will be mutated in some fashion upon homologous recombination. Examples of target nucleic acid sequences include DNA sequences surrounding the tyr 145 UAG amber mutation of galK, as described in Yu et al., *Proc. Natl. Acad. Sci.* 97:5798-5983, 2000, and in Example 3 of this application; the second exon of mouse hox 1.1 gene, as described in U.S. Pat. No.5,464,764; the human hemoglobin S gene mutation as described in Example 15 of published PCT Application No. WO 02/14495 A2, which is herein incorporated by reference.

Targeting frequency: The frequency with which a target nucleic acid sequence undergoes homologous recombination. For example, extrachromosomal DNA is introduced into a eukaryotic cell. The extrachromosomal DNA has sequences capable of undergoing homologous recombination with a target intrachromosomal DNA sequence. After introducing the extrachromosomal DNA and allowing homologous recombination to proceed, the total number of cells may be determined, and the number of cells having the target DNA sequence altered by homologous recombination may be determined. The targeting frequency is the number of cells having the target DNA sequence altered, divided by the total number of cells. For example, if there are a total number of one million cells, and 1,000 of these cells have the target DNA sequence altered, then the targeting frequency is 1 in 1,000, or $10^{-3}$.

Transformed: As used herein, the term transformation encompasses all techniques by which a nucleic acid molecule might be introduced into such a cell, including transfection with viral vectors, transformation with plasmid vectors, and introduction of DNA (including DNA linked to Beta protein) by electroporation, lipofection, and biolistics.

Upstream: Nucleic acid sequences 5' to a nucleic acid sequence of interest. In one embodiment, "upstream" refers to nucleic acid sequences that precede the codons that are transcribed into an RNA of interest. Similarly, downstream refers to nucleic acid sequences 3' of a nucleic acid of interest, such as, but not limited to, a nucleic acid sequence that follows codons that are transcribed into a RNA of interest.

Variants of Amino Acid and Nucleic Acid Sequences: The production of lambda Beta, Exo or Gam, or another ssDNA binding polypeptide can be accomplished in a variety of ways. DNA sequences which encode for the protein, or a fragment of the protein, can be engineered such that they allow the protein to be expressed in eukaryotic cells, bacteria, insects, and/or plants. In order to accomplish this expression, the DNA sequence can be altered and operably linked to other regulatory sequences. The final product, which contains the regulatory sequences and the nucleic acid encoding the therapeutic protein, is operably linked into a vector, allowing stable maintenance in a cell. This vector can then be introduced into the eukaryotic cells, bacteria, insect and/or plant. Once inside the cell, the vector allows the protein to be produced.

One of ordinary skill in the art will appreciate that the DNA can be altered in numerous ways without affecting the biological activity of the encoded protein. For example, PCR may be used to produce variations in the DNA sequence which encodes lambda Beta, Exo or Gam, or other ssDNA binding proteins. Such variants may be variants that are optimized for codon preference in a host cell that is to be used to express the protein, or other sequence changes that facilitate expression.

Two types of cDNA sequence variant may be produced. In the first type, the variation in the cDNA sequence is not manifested as a change in the amino acid sequence of the encoded polypeptide. These silent variations are simply a reflection of the degeneracy of the genetic code. In the second type, the cDNA sequence variation does result in a change in the amino acid sequence of the encoded protein. In such cases, the variant cDNA sequence produces a variant polypeptide sequence. In order to preserve the functional and immunologic identity of the encoded polypeptide, such amino acid substitutions are ideally conservative in highly conserved regions. Conservative substitutions replace one amino acid with another amino acid that is similar in size, hydrophobicity, etc. Outside of highly conserved regions, non-conservative substitutions can more readily be made without affecting function of the protein. Examples of conservative substitutions are shown in Table 1 below.

TABLE 1

| Original Residue | Conservative Substitution |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, should be minimized in order to preserve the functional and immunologic identity of the encoded protein. The immunologic identity of the protein may be assessed by determining whether it is recognized by an antibody to the protein; a variant that is recognized by such an antibody is immunologically, conserved. Particular examples of cDNA sequence variants introduce no more than 20, and fewer than 10 amino acid substitutions, into the encoded polypeptide. Variant amino acid sequences may, for example, be at least 80, 90 or even 95% identical to the native amino acid sequence.

Yeast artificial chromosome (YAC): A vector used to clone DNA fragments (up to 400 kb); it is constructed from the telomeric, centromeric, and replication origin sequences needed for replication in yeast cells (see *Current Protocols in Molecular Biology*, ed. Ausubel et al., Greene Publishing and Wiley-Interscience, New York, 1987 (with periodic updates)).

Wild-type: The genotype or phenotype that is found in nature or in the standard laboratory stock for a given organism.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Recombineering Using Host Cells Deficient for Mismatch Repair

Recombineering, or the use of a recombinase to mediate recombination using homology sufficient to induce recombination, as disclosed herein, can be performed using single-stranded oligonucleotides (oligos) as the targeting cassette. At certain positions on the chromosome, greater than 1% of the SS oligo-treated cells have been shown to be recombinant, making it possible to screen for mutants without using a selectable marker (Ellis et al., *Proc. Natl Acad Sci USA* 98:6742-6746, 2001; Swaminathan et al., *Genesis* 29:14-21, 2001). Single stranded oligos have also been used to effect genetic modifications in yeast (Moerschell et al., *Proc. Natl Acad Sci USA* 85:524-528, 1988; Liu et al., *Mol. Cell. Biol.* 22:3852-3863, 2002; Liu et al., *Nucleic Acids Res* 29:4238-4250, 2001) and in mammalian cells (Gamper et al., *Nucleic Acids Res* 28:4332-4339, 2002; Igoucheva et al., *Gene Ther.,* 8:391-399, 2001). Recombineering can also be performed using double-stranded nucleic acid, or double stranded nucleic acid with a 5' and or a 3' overhang (see published PCT Application No. WO 00214495A2, which is herein incorporated by reference). However, a need remains to increase the frequency of recombination in both eukaryotic and prokaryotic cells. This disclosure provides methods and host cells can be used to increase the efficiency of recombineering.

The recombineering methodology utilizes recombination functions (e.g. phage recombination functions) under control of a de-repressible promoter to generate recombination products using homologies of at least 20 base pairs. Thus, in one embodiment, recombineering uses a cell including Beta under the control of a de-repressible promoter. In specific, non-limiting example, expression of Beta alone (without Exo and Gam) is under the control of the de-repressible promoter (e.g. the nucleic acid encoding Beta is operably linked to the de-repressible promoter). In another embodiment, expression of Beta, in addition to Gam and/or Exo, is under the control of the de-repressible promoter. In further embodiments, RecT, P22 Erf, or Rad52 is operably linked to a de-repressible promoter. In yet another embodiment, DNA bound to a Beta protein is introduced into a host cell.

In recombineering, phage recombination functions can be used to introduce recombination into a target nucleic acid sequence in a host cell. The host cell can be eurkaryotic or prokaryotic. In specific non-limiting examples, the host cell is a mammalian cell, a yeast cell, or a bacterial cell (e.g. *E. coli*). The target can be on the chromosome, or can be on an extra-chromosomal element. In several specific, non-limiting examples, the target nucleic acid can be included in a plasmid, a bacterial artificial chromosome (BAC), a yeast artificial chromosome, a cosmid or a vector, including but not limited to a viral vector. In one specific non-limiting example recombination is induced in a BAC strain or a BAC DNA is introduced into strain carrying recombination functions.

The length of the homologous sequence can be varied. In several embodiments, the homology is at least 20, at least 25, at least 30, at least 40, at least 50, at least 75 or at least 100 nucleotides in length. However, larger regions of homology can also be utilized. Thus, in one embodiment, between about 20 and about 1,000 nucleotides of homologous sequence is utilized, or between about 40 and about 1,000 nucleotides of homologous sequence is utilized. In one specific, non-limiting example, the ssDNA is about 20, about 25, about 30, about 40, about 50, about 75 or about 100 nucleotides in length. In embodiment, the homologous nucleic acid is a single-stranded nucleic acid. In another embodiment, the homologous nucleic acid is a double stranded nucleic acid. Double stranded nucleic acids include molecules that are completely double stranded, as well as nucleic acid molecules that have a 5' or a 3' overhang.

A single-stranded nucleic acid or double-stranded nucleic acid including sufficient homology to the target sequence is introduced into the host cell. "Sufficient homology" is any region of sufficient identity to the target sequence such that recombination can occur. In several embodiments, sufficient homology includes a sequence of at least 20 nucleotides in length, wherein at most five, at most three, at most two, at most one nucleotide, or no nucleotides differ from the target nucleic acid sequence. In additional embodiments, sufficient homology includes a sequence of at least 25 nucleotides in length, wherein at most five, at most three, at most two, at most one nucleotide, or no nucleotides differ from the target nucleic acid sequence. Similarly, sufficient homology can readily be determined for a nucleic acid of at least 30, at least 40, at least 50, or at least 100 nucleotides in length.

If the single-stranded nucleic acid or double-stranded nucleic acid differs from the target nucleic acid, these differences can be clustered (i.e. at one area in the target nucleic acid) or can be scattered in the sequences (e.g. two nucleotide differences from the target sequence, wherein each difference is located at different area in the sequence. In another embodiment, sufficient homology includes about a 100%, 99%, 98%, or 97% sequence identity between the homologous nucleic acid (e.g., the single-stranded or the double-stranded nucleic acid) and the target nucleic acid sequence. In another specific, non-limiting example, sufficient homology includes at least 90% sequence identity between the single-stranded or double-stranded nucleic acid and the target nucleic acid, such as nucleic acid sequences that are at least 91%, at least 92%, at least 93%, at least 94%, at least 95%, at least 96%, at least 97%, at least 98%, or at least 99%, identical. It should be noted that a homologous nucleic acid sequence can differ from a target nucleic acid by substitutions, deletions, and/or additions of nucleotides. In another embodiment, the single stranded nucleic acid (or double-stranded nucleic acid) is labeled, such as with a biotinylated nucleotide, a methylated nucleotide, or a DNA adduct.

The homologous nucleic acid (e.g., the single-stranded nucleic acid or double-stranded nucleic acid) can be introduced into the host cell by any means known to one of skill in the art. As disclosed herein, it is advantageous that the host cell is deficient in mismatch repair. A host cell "deficient" for mismatch repair can repair mismatched nucleotides at a reduced frequency as compared to a wild-type cell, such as at least 50%, 60%, 70%, 80%, 90%, 95%, 98%, or 99% reduction in mismatch repair as compared to a wild-type cell. In one specific, non-limiting example, mismatch repair is reduced at least 90% as compared to a wild-type cell. A host cell deficient for mismatch repair can include a mutation in a nucleic acid sequence encoding a protein involved in mismatch repair, such that the protein has reduced function (or its function is eliminated). Thus, the function. of one or more mismatch repair proteins can be reduced at least 50%, 60%, 70%, 80%, 90%, 95%, 98%, or 99% as compared to the function of the protein in a wild-type cell. In several embodiments, the function of one or more mismatch repair proteins is decreased at least 80%, such as 90%, 95%, 96%, 97%, 98%, 99%, or is completely absent in the host cell deficient for mismatch repair as compared to a wild-type cell. In this context, a wild-type cell is a cell of the same species that does not include a mutation in the gene encoding the protein involved in mismatch repair.

In one embodiment, mismatch repair can be constitutively reduced in the host cell. Thus, if the cell is a prokaryotic cell, a cell that is deficient for mismatch repair can have a mutation in one or more nucleic acids encoding mutS, mutH, mutL, uvrD, or dam. The mutS, mutH, mutL, uvrD, or dam protein produced from the mutated gene has a substantially reduced (or no) function in mismatch repair. Thus, a corresponding wild-type cell does not have a mutation in the nucleic acid encoding MutS, MutH, MutL, uvrD, or dam, respectively. A cell deficient for mismatch repair can also have more than one mutation or the nucleic acid encoding MutS, MutH, MutL, uvrD, or dam, or can have mutations in more than one of these genes. The mutation can be an insertion, deletion, or a point mutation. Thus, in several specific, non-limiting examples, a prokaryotic cell deficient for mismatch repair has a mutation in a nucleic acid encoding Mut S (mutS–, or ΔmutS), MutH (mutH– or ΔmutH), MutL (mutL– or ΔmutL), UvrD (uvrD– or ΔuvrD), or Dam (dam– or Δdam), or a combination (e.g. mutS–mutH–(ΔmutSΔmutH), mutS–mutL–(ΔmutSΔmutL), mutH–mutL–(ΔmutHΔmutL), mutH–uvrD–(ΔmutHΔuvrD), etc.).

The proteins involved in mismatch repair are also known for eurkaryotic cells. Eurkaryotes have proteins with sequence similarity to MutS and MutL that are involved in a similar repair pathway. The eukaryotic MutS is a dimer of MSH2 and GTBP (now known as MSH3 or MSH6) proteins. Eucaryotic mutL also consists of two polypeptides, MLH1 and PMS2. Eukaryotes lack homologs of MutH and uvrD. Exemplary genes encoding mismatch repair proteins are disclosed in the table shown below:

TABLE 2

Genes encoding enzymes of mismatch repair

| E. coli | S. cerevisiae | Human | Functions of Eukaryotic proteins |
|---|---|---|---|
| MutS | MSH1 | ? | DNA repair in mitochondria |
| MutS | MSH2 | MHS2 | Single mismatch and small loop repair (with MSH6 to form MutSalpha); loop repair (with MSH3 to form MutSbeta) |
| MutS | MSH3 | MSH3 | Loop repair (with MSH2 to form MutSbeta) |
| MutS | MSH4 | MSH4 | Meiosis (with MLH1) |
| MutS | MSH5 | MSH5 | Meiosis (with MLH1) |
| MutS | MSH6 | MSH6 | Single mismatch and small loop repair (with MSH2 to form MutSalpha) |
| MutL | MLH1 | MLH1 | Mismatch repair |
| MutL | PMS1 | PMS2 | Mismatch repair (with MLH1 to form MutLalpha) |
| MutL | MLH2 | PMS1 | Interacts with MLH1 to form MutLbeta. Not involved in mismatch repair in yeast. |
| MutL | MLH3 | MLH3 | Loop repair (with MLH1) |
| MutH | ? | — | — |

TABLE 2-continued

Genes encoding enzymes of mismatch repair

| E. coli | S. cerevisiae | Human | Functions of Eukaryotic proteins |
|---|---|---|---|
| uvrD | ? | — | Helicase, generates single strand |
| recJ | Exonuclease 1 | Exonuclease 1 | Mismatch repair (5' to 3' polarity) |
| ? | RAD27 | DNase IV FEN-1 | Mismatch repair (Flap endonuclease) |
| xonA | | | Exonuclease (3' to 5' polarity) |
| dam | — | — | methylase |

It should be noted that *S. pombe* also has two genes encoding MutS functions (MSH2, SW14, and MSH6), two genes encoding MutL functions (MLH1 and PMS1), and an EXO1 gene. *C. elegans* has two genes encoding MutS function (MSH2 and MSH6), and two genes encoding MutL functions (MLH1 and PMS1). *D. melanogasler* has two genes encoding MutS function (SPEL1 and MSH6) and two genes encoding MutL functions (MLH1 and PMS2), and the TOSCA gene. In addition, *A. thaliana* has four genes encoding MutS functions (MSH2, MHS3, MSH6, MSH7), three genes encoding MutL functions (PMS1 and MLH3), and two additional genes involved in mismatch repair (Q9C7N8 and AAK913436, which may be homologous to EXO1) (for review see Marti et al., *J. Cell. Physiol.* 191:28-41, 2002). As disclosed herein, eukaryotic host cell deficient for mismatch repair can have one or more mutations in a gene encoding mismatch repair, or can have mutations in more than one gene involved in mismatch repair.

In another embodiment, the method utilizes a cell that is transiently deficient in mismatch repair. Thus, a cell deficient for mismatch repair can also be a cell treated to inactivate mismatch repair for a specified period of time. In one specific, non-limiting example, a prokaryotic cell (e.g., *E. coli*) can be treated with a compound, such as 2-aminopurine, to induces a reversible phenotype of DNA mismatch repair deficiency (see Matic et al., *J. Bacteriol.* 185:1459-1461, 2003). In another specific, non-limiting example, a cell can be treated with an effective amount of multi-copy single-stranded DNA (see Maas et al., *Molec. Microbiol* 19:505-509, 1996). Multi-copy single-stranded DNA is a single-stranded DNA covalently linked to DNA that forms stem-loop structures. Treatment with multi-copy single-stranded DNA with mismatched base pairs is known to inhibit mismatch repair. Without being bound by theory, this effect is believed to be due to a titration of MutS (see Maas et al, supra, 1996).

In another embodiment, antisense, small inhibitory RNAs, ribozymes, or other nucleotide based strategies are used to induce a decrease in mismatch repair. Antisense nucleic acids are DNA or RNA molecules that are complementary to at least a portion of a specific mRNA molecule (Weintraub, *Scientific American* 262:40, 1990), such a nucleic acid encoding a protein involved in mismatch repair. In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, *Anal. Biochem.* 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher et al., *Antisense Res. and Dev.* 1:227, 1991; Helene, *Anticancer Drug Design* 6:569, 1991), such as a gene encoding a protein involved in mismatch repair.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.* 260:3030, 1988). A major advantage of this approach is that, because they are sequence-specific, only mRNAs with particular sequences are inactivated.

There are two basic types of ribozymes namely, *tetrahymena*-type (Hasselhoff, *Nature* 334:585, 1988) and "hammerhead"-type. *Tetrahymena*-type ribozymes recognize sequences which are four bases in length, while "hammerhead"-type ribozymes recognize base sequences 11-18 bases in length. The longer the recognition sequence the greater the likelihood that the sequence will occur exclusively in the target mRNA species. Consequently, hammerhead-type ribozymes are preferable to *tetrahymena*-type ribozymes for inactivating a specific mRNA species and 18-based recognition sequences are preferable to shorter recognition sequences.

A "transfected cell" or a "transformed cell" is a cell into which has been introduced, by means of recombinant DNA techniques, a nucleic acid molecule. The nucleic acid molecule can be single-stranded or double-stranded (including a double-stranded nucleic acid with an overhang). The introduction of a nucleic acid molecule into a host cell can be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences including sequence of interest, and a second foreign DNA molecule encoding a selectable phenotype, such as neomycin resistance (see for example, *Eukaryotic Viral Vectors*, Cold Spring Harbor Laboratory, Gluzman ed., 1982). Other specific, non-limiting examples of viral vectors include adenoviral vectors, lentiviral vectors, retroviral vectors, and pseudorabies vectors.

The homologous nucleic acid (e.g. the single-stranded nucleic acid or double-stranded nucleic acid) is introduced into the host cell deficient for mismatch repair, the de-repressible promoter is activated, and recombinants are generated in vivo. Thus, in one specific, non-limiting example, if the de-repressible promoter is PL, the host cell is treated with heat to induce the expression of Beta (see Copeland et al., *Nature Reviews* 2:769, 2001, and Ellis et al., *Proc. Natl. Acad. Sci.* 98:6742-6746, 2001, which are herein incorporated by reference). Generally, the homologous nucleic acid, whether it is a single-stranded nucleic acid or a double-stranded nucleic acid, differs from the target nucleic acid by at least one nucleotide, but is sufficiently homologous to undergo recombination with the target sequence (see above).

Recombinants can be detected by any means known to one of skill in the art. If recombination has occurred in a nucleic acid encoding a marker, such as a nucleic acid encoding a polypeptide involved in antibiotic resistance, detection can be performed by selection or counterselection. However, detection can also be performed by direct screening (e.g. colony hybridization or sequencing). Detection can also be performed by detecting a label on the nucleic acid (e.g. when DNA includes a DNA adduct or a marker such as biotin).

As has been described in *E. coli* (see published PCT application No. WO 02/14495 A2, herein incorporated by reference), a single base change has been substituted in the galK gene and a 3.3 kbp insertion removed from the galK gene using single-stranded oligos. Single-stranded oligos have also been used to cure 5 different Tn10 insertions at different places on the *E. coli* chromosome. Whereas Exo,.Beta, and Gam facilitate recombination of PCR amplified dsDNA cassettes with flanking homologies, only Beta is required for ssDNA recombination.

Recombination with either of two complementary DNA oligos has revealed that although either strand can be efficiently used for recombination, one strand is more competent for recombination than the other. This strand bias has been examined at several positions around the bacterial chromosome with the result that the preferred strand correlates with the lagging strand of DNA replication for each site tested. Without being bound by theory, these results indicated that strand bias is associated with the replication direction through the region being targeted and that ssDNA recombination occurs efficiently near the replication fork. The process of DNA replication results in transient regions of ssDNA that may be accessible to Beta-mediated annealing of the ssDNA oligo. Although recombination occurs on the leading strand, the increased recombination efficiency of the lagging strand oligos could reflect the increased frequency of single-stranded regions during lagging versus leading strand synthesis. DNA polymerase and DNA ligase could then complete the joining of the annealed oligo to the lagging strand (see PCT application No. WO 00214495 A2, which is herein incorporated by reference). Without being bound by theory, mutations in a mismatch repair protein, such that mismatch repair is reduced in the host cell, do not change the stand bias for recombination of single stranded DNA. However, a deficiency in mismatch repair results in an increased detection of recombinants, whether a recombination occurs with the leading or the lagging strand of the target double-stranded DNA (see FIG. 1).

Figure 2:
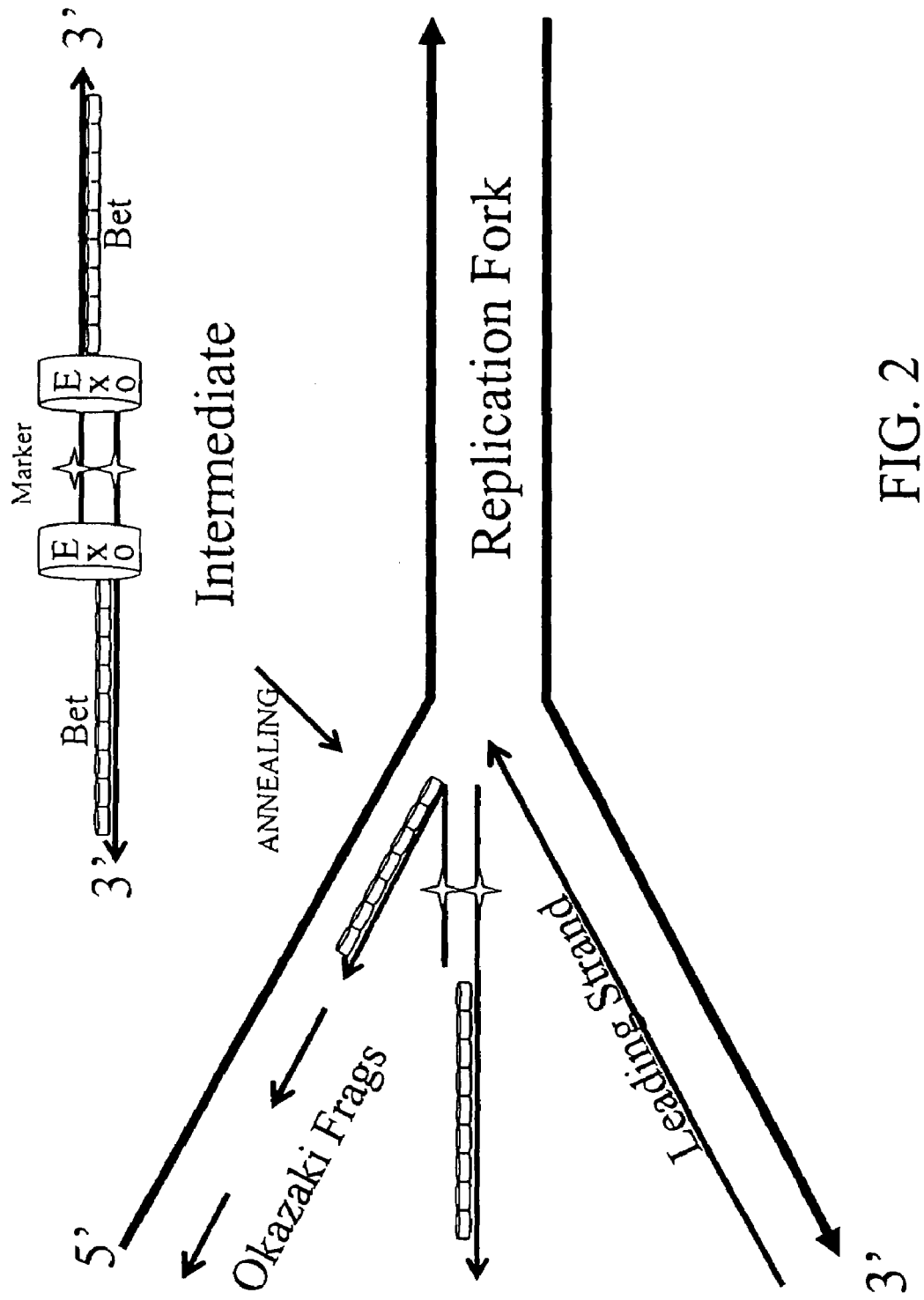
FIG. 2 is a schematic diagram of the use of a double stranded DNA including a 3' overhang. Two single stranded oligonucleotides are generated that are homologous to each other over a portion of their sequence, and thus can form an intermediate that is a double-stranded nucleic acid with 3' overhangs. The overhangs are single stranded. Beta (bet) binds the single-stranded ends of the intermediate, and can mediate recombination of this molecule into a target sequence. The annealing of intermediate to the replication fork at the lagging strand is shown.
Figure 3:
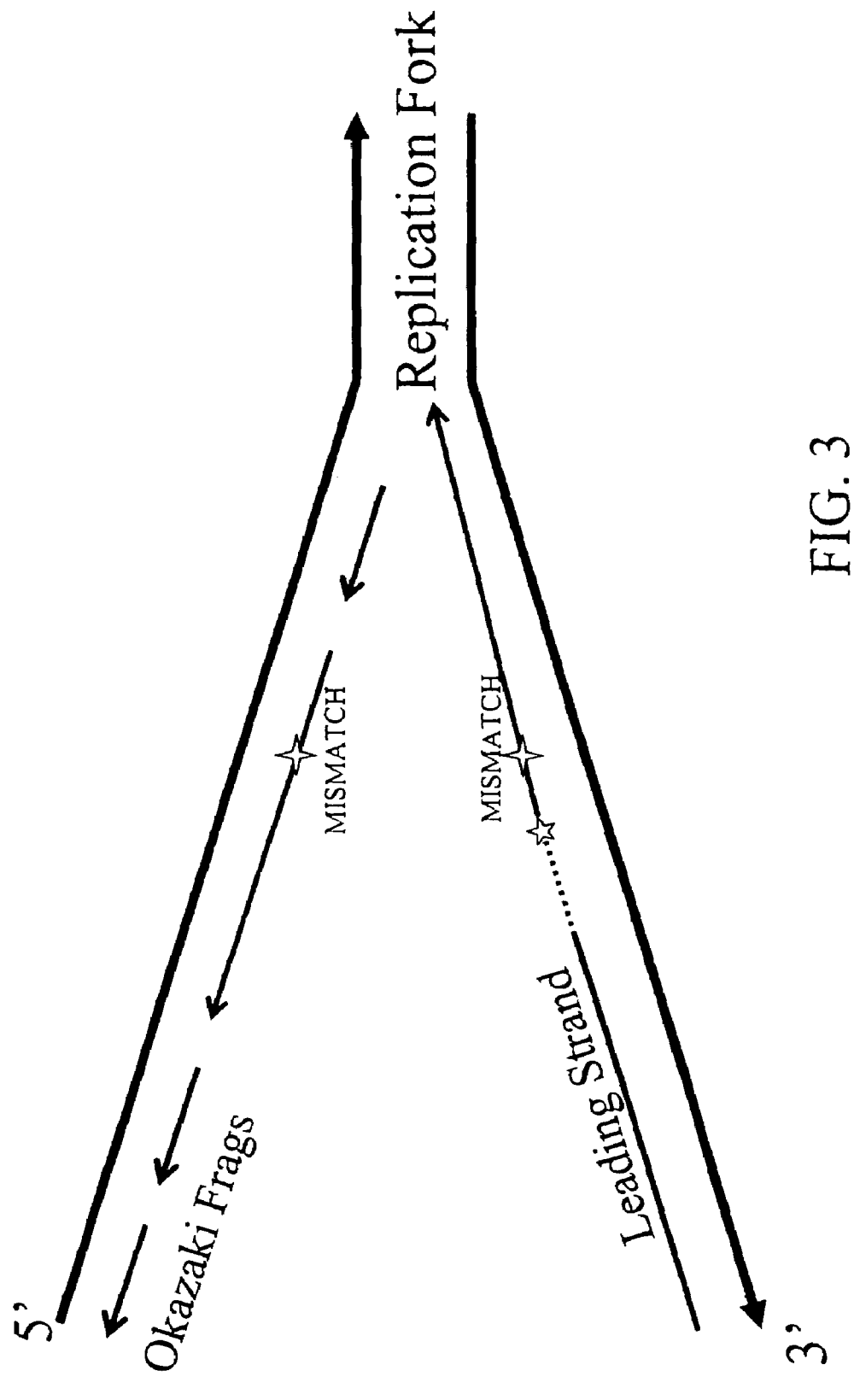
FIG. 3 is a schematic diagram of branch migration at a replication fork that occurs following the step shown in FIG. 2. A region of mismatch is indicated. The mismatch repair proteins will correct the mismatch. Thus, recombination frequency will be increased in a host cell that is deficient for mismatch repair.

FIG. 1 shows is a schematic diagram of repair of a mismatch when single-stranded nucleic acid is utilized. When double-stranded DNA that does not include 3' or 5' overhangs is used for linear recombination, exo, bet, and gam gene products are required. However, when single stranded nucleic acid, or when double-stranded nucleic acid with a 3' and/or 5' overhang is utilized, only Beta is required. Without being bound by theory, a DNA structure is suggested that is shown in the top of FIG. 2. In this model, a linear double-stranded DNA with flanking 3' single-stranded DNA overhangs is generated as an annealing intermediate with Beta bound. Such a structure made in vitro and electroporated into a cell is recombinogenic; this recombination does not require Exo. Experiments have been performed in which the 3' overhangs were constructed by co-electroporating two oligonucleotides that are 70 nucleotides in length that pair only in the middle. As predicted by the model shown in FIG. 2, this substrate recombined and more importantly, required only Beta. The presence or absence of Exo had no effect. This recombination was also found to be recA-independent. Because single-stranded DNA ends are involved, this intermediate, like single stranded DNA, is likely to initiate recombination at a DNA replication fork (FIGS. 2 and 3). A mismatch may be left in both daughter DNA molecules.

Cells of Use

Isolated host cells of use in the methods disclosed herein include a de-repressible promoter operably linked to a nucleic acid encoding a recombinase. These cells are also deficient for mismatch repair. In one embodiment, the cell is constitutively deficient for mismatch repair. The cell can be a eukaryotic cell or a prokaryotic cell. In one embodiment, the cell is a bacterial cell, such as a gram positive or a gram negative bacterial cell. In one specific, non-limiting example, the bacteria is a gram negative bacteria, such as an enteric bacteria (e.g. *E. coli*). In another embodiment, the cell is a eukaryotic cell. Thus, the cell can be a yeast cell or a mammalian cell. Other specific, non-limiting examples, the cell can be a *S. cerevisiae* cell, and *S. pombe* cell, a *C. elegans* cell, a *D. nielanogaster* cell, an *A. thaliana* cell, a murine cell, or a human cell.

Thus, in one embodiment, the cell has a mutation in a gene encoding a protein of mismatch repair (see Table 2), in addition to including a de-repressible promoter operably linked to a nucleic acid encoding a recombinase. Mutations in a gene encoding the mismatch repair protein can be made or selected by any means known to one of skill in the art. Methods for introducing a mutation in a gene, or for "knocking out" a gene are known for both prokaryotic and eurkaryotic cells (see for example, *Molecular Cloning: A Laboratory Manual*, 2nd ed., vol. 1-3, ed. Sambrook et al., Cold Spring Harbor Laboratory Press, Cold Spring Harbor, N.Y., 1989, and *Current Protocols in Molecular Biology*, ed. Ausubel et al., Greene Publishing and Wiley-Interscience, New York, 1987 (with periodic updates)).

Targeted disruption of a gene in vivo with complete loss of function has been achieved by any transgenic technology familiar to those in the art. In one embodiment, gene knockouts are utilized in which a target gene has been rendered nonfunctional by an insertion targeted to the gene to be rendered non-functional by homologous recombination. As used herein, the term "transgenic" includes any transgenic technology familiar to those in the art which can produce a cell or an organism carrying an introduced transgene or one in which an endogenous gene has been rendered non-functional or knocked out.

In one specific, non-limiting example, a specific mutation is introduced into a mismatch repair gene in the host cell. In another embodiment, the entire gene may be deleted. Optionally, a disruption or deletion in a gene encoding a protein involved in mismatch repair may be accompanied by insertion of or replacement with other DNA sequences, such as a nucleic acid encoding a selectable marker (such as, but not limited to, an nucleic acid conferring resistance to an antibiotic). In other embodiments, the host cell includes a DNA antisense to the coding sequence for the nucleic acid encoding the mismatch repair protein, or a ribozyme that specifically targets the nucleic acid encoding a mismatch repair protein.

In one embodiment, a gene encoding mismatch repair (e.g. see Table 2 above) is disrupted by homologous targeting in a eurkaryotic cell. These include lower organisms such as yeasts, slime molds, and the like, as well as cells from multicellular organisms such as invertebrates, vertebrates, and mammals. Suitable cells include, but are not limited to, stem cells such as hematopoietic progenitor cells, hematopoietic stem cells, and embryonic stem cells. Suitable cells also include differentiated cells, including tumor cells and cell lines. The cell can be a terminally differentiated cell, such as a differentiated cell from any organ, including but not limited to cells from the circulatory system, respiratory system, reproductive system, lymphoid organs, excretory system. These include cells in a variety of tissue types, such as: endothelial cell, smooth muscle cell, epithelial cell, hepatocyte, cells of neural crest origin, tumor cell, hematopoietic cell, lymphoid cell, T cell, B cell, monocyte, macrophage, dendritic cell, fibroblast, keratinocyte, neuronal cell, glial cell, adipocyte, myoblast, myocyte, chondroblast, chondrocyte, osteoblast, osteocyte, osteoclast, secretory cell, endocrine cell, oocyte, and spermatocyte.

In another embodiment, the cell is a prokaryotic cell. Thus, in one specific, non-limiting example, the cell is a gram negative bacteria, such as, but not limited to, an enteric bacteria. Thus, in one specific, non-limiting example the cell is an $E.$ $coli$ cell that is deficient for mismatch repair and includes a nucleic acid encoding a single-stranded binding protein, operably linked to a de-repressible promoter. In one embodiment the single-stranded binding protein is Beta. The cell can optionally also include a nucleic acid sequence encoding Exo and/or Gam.

The bacterial cell can be generated using a mini-lambda (see PCT WO 02/14495 A2, which is herein incorporated by reference). Thus, in this embodiment, the host cell is deficient for mismatch repair and includes a mini-lambda. In another specific, non-limiting example, the cell is an isolated bacterial cell comprising a defective lambda prophage of genotype $\lambda$cI857 $\Delta$(cro-bioA), wherein the bacterial cell further comprises a mutation in at least one nucleic acid sequence encoding a mismatch repair polypeptide. Thus, in addition to including a de-repressible promoter operably linked to a nucleic acid encoding a recombinase (e.g. encoding Beta), the bacterial cell also includes a mutation in one or more of MutS, MutH, MutL, uvrD, and/or dam. Methods for introducing mutations in a bacterial cell are well known in the art (e.g. see Yu et al. $Proc.$ $Natl$ $Acad.$ $Sci.$ $USA$ 97:5978-5983, 2000, herein incorporated by reference), and exemplary methods are disclosed in the examples section below). The isolated bacterial cell can have mutations in two or more of these genes. Thus, in several specific, non-limiting examples, a prokaryotic cell deficient for mismatch repair has a mutation in two or more of MutS (MutS−), MutH (mutH), MutL (mutL−), uvrD (uvrD−), or dam (dam−), for example, the cell is an isolated bacterial cell having a MutS−MutH−, MutS−MutL−, MutH−MutL−, or a MutH−uvrD−, genotype. In bacterial cells, there are additional proteins that have one or more functions of the dam methylase. Thus, suitable host cells can also include mutations in additional genes that encode polypeptides with a dam methylase function. Thus, in one specific, non-limiting example, the host cell includes mutation in a gene encoding a polypeptide with a dam methylase function (that is not dam), one or more mutations in MutS, MutH, MutL, or uvrD, and/or dam. In another specific non-limiting example, the host cell includes a mutation gene encoding a polypeptide with a dam methylase function that is not dam, and a mutation in dam.

In another specific, non-limiting example the bacterial cell can be derived from HME6, DY380 or a DY330 cell, such that a mutation is introduced into a gene encoding a protein involved in mismatch repair. One of skill in the art can readily produce these cells using known methods. The generation of several exemplary cells, and the genotype of these cells, is disclosed in the Examples section below (e.g., see Tables 3 and 7).

Exemplary bacterial strains have been deposited as ATCC No. PTA-5184 (HME6 (Mut+)), ATCC No. PTA-5187 (HME63 (MutS)), ATCC No. PTA-5185 (HME 61 (MutH)), ATCC No. PTA-5186 (HME62 (MutL)), and PTA-5188 (HME64 (uvrD)), all of which were deposited on May 8, 2003.

These cells, and exemplary specific methods to produce cells deficient in a protein involved in mismatch repair, are further described in the Examples below.

The disclosure is illustrated by the following non-limiting Examples.

EXAMPLES

Example 1

Materials and Methods

The lambda Red recombination system has been extensively used to modify the bacterial chromosome with single-strand oligonucleotides (ss oligo). As shown previously, a strand bias of the ss oligo can be demonstrated with regards to chromosome replication but not to transcription direction. Both the host MMR system and sequence of the single-strand oligonucleotide play an important role when a single base change is repaired.

Single-strand DNA oligonucleotides (ss oligos) have been used to modify the chromosome in both yeast and $E.$ $coli$ (Ellis et al., $Proc.$ $Natl.$ $Acad$ $Sci.$ $USA$ 98:6742-6746, 2001). The lambda Red recombination system has been used with ss oligos to create mutations, to correct single base mutations, to create deletions, and to remove large heterologies from the $E.$ $coli$ chromosome. The $\lambda$ Red system includes the Beta, Exo and Gam proteins. However, recombination with ss oligos requires only the Beta function. Oligos with homologies as short as 20 bases can be used to recombine in $E.$ $coli$ and as little as 10 ng of oligo yields saturating levels of recombinants (Ellis et al., supra).

For any allele the oligo corresponding to either of the two complementary strands carrying that allele can be used to initiate recombination. For several cases tested, there was a marked strand bias for one of the two complementing oligos used as a recombination substrate (Ellis et al., supra). This strand preference appeared to be correlated to the direction of DNA replication through the region being recombined; the direction of transcription through the allele did not appear to cause the bias. As disclosed herein, the primary bias observed is not caused by transcription but is determined by the direction of DNA replication.

Beta can anneal complementary strands but cannot cause a ssDNA to invade a duplex DNA; RecA function can cause strand invasion but is not required for Beta-mediated recombination. Therefore, Beta-mediated recombination with a ss oligo is likely to be directed to a single-strand region of the chromosome. A DNA replication fork provides an ideal area of the chromosome with exposed single-strand regions. The strand bias observed for oligo recombination is dependent upon replication direction. The oligo that corresponds in sequence to Okazaki fragments generates the highest efficiency. Such oligos are referred to herein as the lagging strand oligo and their complement as the leading strand oligo with reference to the replication fork.

Many host proteins are involved in progression of the replication fork. As disclosed herein, a decrease in the proofreading system of methyl-directed mismatch repair (MMR) results in an increase in recombinant yield when a ss oligo is utilized. The host MMR system acts to correct small base pair mismatches by first recognizing, then excising the incorrect base. Without being bound by theory, the changes that the ss oligos introduce at the replication fork may trigger mismatch repair. Thus, decreasing MMR can affect the frequency that homologous recombination can be detected. The following material and methods were used in the Examples.

Genotype of strains: HME5 is W3110 Δ(argF-lac)U169 gal+, {λcI857 Δcro-bioA}. HME6 is HME5 galK tyr145UAG, HME31 is HME5 galK<>cat-sacB, and HME41 is HME6 with the entire gal operon inverted without inverting the adjacent genes. These strains have previously been described (Ellis et al., supra). HME6, HME31, and HME41 were made recA− by P1 transduction to move in Δsrl-recA:: Tn10.

Deletion of host factor genes: Host MMR genes mutH, mutL, mutS, uvrD, and dam were inactivated by inserting PCR generated antibiotic resistant cassettes in place of the coding region of each gene (see Table 3 below).

TABLE 3

Knock outs of methyl-directed mismatch repair genes[1]

| | |
|---|---|
| dam<>kan | (5'dam AGGGGGCAAGTA-kan-TTCTCAAGGAGA 3'dam) |
| | (5'dam SEQ ID NO: 1-kan-SEQ ID NO: 2-3'dam) |
| mutH<>amp | (5'mutH AGGTATCATGAC-amp-AGTGCACTACTG 3'mutH) |
| | (5'mutH SEQ ID NO: 3-amp-SEQ ID NO: 4-3'mutH) |
| mutL<>amp | (5'mutL CAACTGGCGAAC-amp-TACATCCGGCGA 3'mutL) |
| | (5'mutL SEQ ID NO: 5-amp-SEQ ID NO: 6-3'mutL) |
| mutS<>amp | (5'mutS GGACATAACCCC-amp-TAATAACAATTC 3'mutS) |
| | (5'mutS SEQ ID NO: 7-amp-SEQ ID NO: 8-3'mutS) |
| uvrD<>kan | (5'urvD GGACGTTTCTTA-kan-TAACGTTGCCGG 3'mutS) |
| | (5'urvD SEQ ID NO: 9-kan-SEQ ID NO: 10-3'mutS) |

[1]Sequence in capital letters indicates chromosomal regions near the designated gene that flank the inserted antibiotic cassette.

Either a kanamycin or ampicillin resistance cassette was amplified by PCR using oligos that contained at their 5' ends 45-55 bases of homologies to the target MMR gene. The PCR cassettes with flanking homologies were used for recombination (Yu et al., Proc. Natl. Acad. Sci. USA 97:5978-5983, 2000); recombinants were selected for antibiotic resistance and tested by analytical PCR. Once the substitution was confirmed, it was moved by P1 transduction into the appropriate strains.

E. coli transformation: Electroporation-competent cells were prepared according to Yu et al., Proc. Natl Acad. Sci. USA 97:5978-5983, 2000, herein incorporated by reference. Briefly, overnight cultures inoculated from a single colony were diluted 50-fold in LB medium (total volume 10 ml), and grown to $OD_{600}$=0.6. Expression of Red functionality was then induced by shifting the cells to 42° C. for 15 minutes followed by chilling on ice for 20 minutes. Cells were harvested by centrifugation, washed with ice-cold sterile water (3×1.5ml). The cell pellets were then resuspended in sterile water (50 μl) and transformed with DNA by electroporation at 1.75 kV, 25 mF using the E. coli Pulser (BIO-RAD). LB-media (1 ml) was added then the cells were incubated at 32° C. for 1.5 hours with shaking, before being spread onto the appropriate selective LB-agar media plates or minimal galactose (see Ellis et al., Proc. Natl Acad. Sci. USA 98:6742-6746, 2001).

Materials: Oligonucleotides and PCR primers were supplied by Invitrogen as salt free but otherwise not purified. All ss oligos used to correct the galK mutations were 70 bases in length. The sequence of Oligo 100 which corrects the TAG stop to a TAT tyrosine codon is: 5' AAGTCGCGGTCG-GAACCGTATTGCAGCAGCTTTATCATCT-GCCGCTGGAC GGCGCACAAATCGCGCTTAA 3' (SEQ ID NO: 11). Oligo 101 is the complementary strand to 100. Oligos 144 and 145 were identical to 100 and 101 respectively except that they correct the TAG stop to a TAC tyrosine codon. The detailed sequence of these ss oligos around the galK amber stop is shown in Example 2. Taq polymerase HiF and Concert Rapid PCR purification kits were supplied by Invitrogen.

Assay for recombination to gal+ phenotype: Strains were induced at 42° C. for 15 minutes to express λ Red functions and immediately made electro-competent as previously described (Yu et al., Proc. Natl. Acad. Sci. USA 97: 5978-5983, 2000). Saturating levels (100 ng) of each ss oligo were used per electroporation. Gal+ recombinant colonies were selected on minimal galactose plates and viable cells were counted on L plates as described previously (Ellis et al., 2000, supra).

Plasmid construction, p(+)mKan and p(−)mKan: DNA inserts for the plasmid constructs were amplified by PCR with Expand High-fidelity polymerase using primers containing restriction enzyme sites suitable for cloning. All inserts were sequenced to check for possible mutations introduced by PCR. Primers mKan-1: 5'-GGTTCTCCGGCCGCT-TGGGTGGAGAGGCTATTCGGCTAGGACTG-3', SEQ ID NO: 12 and mKan-2 5'-TATTCGGCAAGCAGGCATCG-3', SEQ ID NO: 13 were used to amplify a 559 bp fragment from plasmid pGK-frt. The EagI-NcoI digested 559 bp PCR fragment was then ligated into the 4,287 bp EagI-NcoI fragment from pGK-frt to form pmKan. To construct p(+)mKan and p(−)mKan, the purified EcoRI-ClaI fragment from pmKan was ligated to the 2942 bp EcoRI-ClaI fragment of pBSKS and pBSSK to form p(+)mKan and p(−)mKan, respectively.

Construction of additional mutants: To construct E. coli strain DY380(+), PCR was used to amplify a 2,397 bp fragment from p(+)mKan using the primers DY380(+)-1
(GGCGCTGCAAAAATTCTTTGTCGAACAGGGTG    SEQ ID NO; 14)
TCTGGATCTAATGCGCCGCTACAGGGCGCGTAA, and DY380(+)-2
(GGCGCTGCAAAAATTCTTTGTCGAACAGGG    SEQ ID NO: 15)
TGTCTGGATCTAATGCGCCGCTACAGGGCGCGTAA, The purified PCR fragment, which contained the mKan gene and an Amp selectable marker flanked by two regions homologous to the chromosomal target, was inserted into DY380 via Red-mediated homologous recombination as described previously (Yu et al. Proc. Natl Acad. Sci. USA 97:5978-5983, 2000; Ellis et al., Proc. Natl Acad. Sci. USA 98:6742-6746, 2001). The recombination event inserts the drug cassettes between the λ prophage cro gene and the bioA gene adjacent to the prophage (see Lee et al., Genomics 73:56-65, 2001). Amp$^r$ colonies were selected then screened by PCR, using the primers DY380(+)detect (ACGT-TAAATCTATCACCGCAAGGG-3', SEQ ID NO: 16) and PGK-frt-2 (5'-TATTCGGCAAGCAGGCATCG-3', SEQ ID NO: 17) to positively identify those that contained the correctly inserted cassettes. Similarly, the other mutant strains were generated by Red-mediated recombination using appropriate PCR-generated cassettes. The normal and inverted gal operon with the galKam mutation have been described by Ellis et al., *Proc. Natl Acad. Sci. USA* 98:6742-6746, 2001.

TABLE 4

Additional Bacterial strains

| Strain | Genotype |
|---|---|
| DH10B | F$^-$ mcrA Δ (mrr-hsdRMS-mcrBC) φ80dlacZΔ M15 Δ lacX74 deoR recA1 endA1 araD139 Δ (ara, leu) 7649 galU galK rspL nupG |
| DY330 | W3310 ΔlacU169 gal490 λcI857 Δ (cro-bioA) |
| DY380 | DH10B [λcI857 (cro-bioA) < >tet][a] |
| DY330(+) | DY330 [(cro-bioA) < >(mKan-Amp$^r$)] |
| DY330(-) | DY330 [(cro-bioA) < >(Amp$^r$-mKan)][b] |
| DY380(+) | DY380 [(cro-bioA) < >(mKan-Amp$^r$)] |
| DY380(-) | DY380 [(cro-bioA) < >(Amp$^r$-mKan)][b] |
| DY380ΔmutS | DY380 [mutS< > Cm$^r$] |
| DY380(+)ΔmutS | DY380(+) [mutS< > Cm$^r$] |
| DY380(-)ΔmutS | DY380(-) [mutS< > Cm$^r$] |
| DY380(+)ΔmutL | DY380(+) [mutL< > Cm$^r$] |
| DY380(-)ΔmutL | DY380(-) [mutL< > Cm$^r$] |
| DY380(+)ΔmutH | DY380(+) [mutH< > Cm$^r$] |
| DY380(-)ΔmutH | DY380(-) [mutH< > Cm$^r$] |
| DY380(+)Δmfd | DY380(+) [mfd< > Cm$^r$] |
| DY380(-)Δmfd | DY380(-) [mfd< > Cm$^r$] |
| DY380(+)ΔuvrB | DY380(+) [uvrB< > Cm$^r$] |
| DY380(-)ΔuvrB | DY380(-) [uvrB< > Cm$^r$] |
| HME6 | W3310 galK$_{tyr145UAG}$ λcI857 Δ (cro-bioA) |
| HME41 | W3310 INgal < > (galM$^+$ K$_{tyr145UAG}$ T$^+$ E$^+$) λcI857 Δ (cro-bioA)[c] |

[a]The symbol < > indicates a replacement generated by recombineering technology. For example, (cro-bioA) < > tet indicates the substitution of cro-bioA with tet.
[b]mKan-Amp$^r$ and Amp$^r$-mKan indicates that the mKan gene has been inserted in opposite directions in the two DY380 or DY330 strains.
[c]INgal indicates that the gal gene has been inserted in opposite directions in the HME6 strain.

Deletion of the mfd or uvrB genes (i.e. strains defective in TCR) led to only minor changes in the recombination efficiency. By deleting mfd or uvrB genes, it was demonstrated that the transcription-coupled repair pathway does not affect for Red/SSO-mediated recombination. As disclosed herein, SSO mediate recombination even in recA and mutS double mutant strains.

Example 2

Sequence Affects Recombination Efficiency

Oligo 100 and its complement 101 are designed to correct the galK$_{tyr145am}$ to the original TAT tyrosine codon. Two other oligos are also made to correct the galK mutation but to a different tyrosine codon; Oligo144 and its complement 145 create a TAC tyrosine codon (see below).

| OLIGO 100 | | CAG CTT TAt CAT CTG | (SEQ ID NO: 18) |
| | 5' | or | |
| OLIGO 144 | | CAG CTT TAc CAT CTG | (SEQ ID NO: 19) |
| | 5' | CAG CTT TAG CAT CTG 3' | (SEQ ID NO: 20) |
| | 3' | GTC GAA ATC GTA GAC 5' | (SEQ ID NO: 21) |
| OLIGO 101 | | GTC GAA ATa GTA GAC | (SEQ ID NO: 22) |
| | | or 5' | |
| OLIGO 145 | | GTC GAA ATg GTA GAC | (SEQ ID NO: 23) |

In these sequences, the G:C pair which creates an amber codon is shown in bold. The correcting base brought in by the repair oligos is shown in lower case.

Although Oligos 100 and 101 generate many gal$^+$ recombinants, the relative efficiency of Oligo 144 recombination was much greater than that for Oligo 100 and Oligo 101 (see Table 5 below).

TABLE 5

Oligo differences in recombination frequency

| Strain | galK gene | oligo | DNA replic | Gal+ recombinants |
|---|---|---|---|---|
| HME6 | amber | 100 | lagging | $2.9 \times 10^5$ |
| | | 144 | lagging | $4.7 \times 10^7$ |
| | | 101 | leading | $4.3 \times 10^4$ |
| | | 145 | leading | $1.8 \times 10^4$ |
| HME31 | <>cat sacB | 100 | lagging | $1.2 \times 10^5$ |
| | | 144 | lagging | $9.5 \times 10^4$ |
| | | 101 | leading | $3.5 \times 10^3$ |
| | | 145 | leading | $2.0 \times 10^3$ |

The frequency of Gal$^+$ recombinants with Oligo 144 was $4.7 \times 10^7$, approximately 100-fold greater than for Oligo 100, which is identical except for the one base difference in the tyrosine codon. On the other hand, the frequency recombinants with Oligo 145 were similar to that of Oligo 101.

Oligo 144 and Oligo 145 correct galK< >cat-sacB with the same efficiency as Oligo 100 and Oligo 101, respectively. Thus, Oligo 144 yields a dramatic increase in recombinant yield with the galK$_{tyr145am}$ point mutant but the same enhanced effect is not provided during recombination with the cat-sacB heterology containing the 3.3 kbp insertion in galK. This result suggests that the pairing difference of Oligo 100 and Oligo 144 with the complementary strand of the galK$_{tyr145am}$ mutation might generate the differences in recombination efficiency observed.

The Oligo 100 TATsequence generates a T/C mismatch whereas the Oligo 145 TAC sequence generates a C/C mismatch. The MutS protein of the methyl-directed mismatch repair (MMR) system binds and corrects T/C as well as most other single base mismatches but does not bind and correct C/C mismatches. This suggests that C/C mismatch can be used to generate changes in a target nucleic acid sequence by homologous recombination using this system. The MMR system does not recognize mismatches created between large heterologies like those expected for cat-sacB repair by the oligos. Thus, the low efficiency of repair of cat-sacB by these oligos is caused by an intrinsically poor recombination rate relative to that of the point mutation. This indicates that mismatch repair corrects base pair mismatches inserted during homologous recombination.

Example 3

Mismatch Repair Genes are Important in Correcting $galK_{tyr145am}$ but Not cat-sacB The effect of recombination by the components of the MMR system was tested in an HME6 background (see Table 3, above). These strains were used to test the ability of the lagging strand Oligo 100 and leading strand Oligo 101 to correct the amber mutation. For both oligos, elimination of the mutH, mutL, mutS, or uvrD genes also increases recombination efficiency by ~100-fold (Table 6).

TABLE 6

Effect of MMR genes on Recombination with point and insertion mutations Gal+ recombinants[2]

| MMR | HME6 (amber) | HME31 (cat-sacB__) |
|---|---|---|
| wild-type | $4.7 \times 10^5$ | $1.2 \times 10^5$ |
| ΔmutH | $2.1 \times 10^7$ | $5.2 \times 10^4$ |
| ΔmutL | $2.2 \times 10^7$ | $1.0 \times 10^5$ |
| ΔmutS | $3.6 \times 10^7$ | $1.4 \times 10^5$ |
| ΔuvrD | $2.7 \times 10^7$ | not done |
| Δdam | $2.7 \times 10^6$ | $1.6 \times 10^5$ |

[2]Data is given from single experiments and wild-type data falls within the expected values based on mean and standard deviation from Table 5.

A Dam methylase mutant was also tested that was created (dam< >amp). In the HME6 dam< >amp strain only a 10-fold increase in recombination efficiency was observed relative to HME6. In other mismatch repair mutants there is a 100-fold effect. This suggests that there is a redundancy in recognizing the parental strand. Additional mutations in proteins involved in this recognition could also be used to increase recombination frequency. Comparable increases in efficiency were also seen when the complementary Oligo 101 was used. However, the MMR deficient strains did not show a difference in recombination frequency when either Oligo 100 or 101 was used to remove the large heterology, cat-sacB.

Example 4

Replication Bias is Independent of Oligo Sequence and Deletion of mutS Gene Product Eliminates Oligo Sequence Bias The four ss oligos were tested in strains HME6 and HME41, both of which contain the $galK_{tyr145am}$. Because these strains are identical, except for the orientation of the gal operon, the recombination efficiency can be examined for each oligo when it acts as either a lagging or leading strand oligo. As can be seen in Table 7, each oligo gives a higher recombination frequency when it acts as the lagging strand oligo irrespective of the presence or absence of the MMR system.

TABLE 7

Recombination at galK amber - sequence and mutS effect[3]

| | Gal+ Recombinants | | | |
|---|---|---|---|---|
| | Wild-type | | ΔmutS | |
| Oligo | Lagging | Leading | Lagging | Leading |
| 100 | $4.7 \times 10^5$ | $1.1 \times 10^4$ | $3.6 \times 10^7$ | $1.4 \times 10^6$ |
| 101 | $\underline{1.6 \times 10^6}$ | $\underline{4.8 \times 10^4}$ | $\underline{5.5 \times 10^7}$ | $\underline{2.1 \times 10^6}$ |
| 144 | $\underline{5.2 \times 10^7}$ | $1.3 \times 10^6$ | $\underline{5.1 \times 10^7}$ | $8.9 \times 10^5$ |
| 145 | $8.1 \times 10^4$ | $\underline{1.0 \times 10^4}$ | $3.0 \times 10^7$ | $\underline{2.1 \times 10^6}$ |

[3]Values underlined were obtained in strain HME41, gal operon inverted. The two strains HME6 and 41 are identical except that gal is precisely inverted in 41. Thus, replication that reaches the gal operon passes through gal in different relative directions in the two strains. In HME 6 the oligos of 100 and 144 are the same as the Okazaki fragments whereas in HME41 they are the same as the leading strand DNA. This is reversed for the oligos 101 and 145. As both strains were utilizedall combinations were tested. In a strain including the mutS deletion, the effects of sequence are eliminated.

As shown in Table 7, the variability in lagging strand recombination is broad in MMR proficient strains, ranging from $8 \times 10^4$ to $5 \times 10^7$, depending on which oligo is used. Diversity in recombination efficiency is also observed with the leading strand where values range from $1 \times 10^4$ to $1 \times 10^6$. Thus it was determined if these variations would persist in a strain deficient for MMR. Therefore all four oligos were tested in both HME6mutS< >amp and HME41mutS< >amp.

The recombination efficiency for lagging strand oligos, regardless of the mismatch created, is approximately $4 \times 10^7$ in the mismatch deficient strains. The recombination with leading strand oligos is also more uniform, averaging $1.6 \times 10^6$. Beta alone in a strain defective for the exo and gam genes gave the same number of recombinants in both mut+ and mutS strains when the ssDNA corresponded to the lagging strand, whereas the when the ssDNA corresponded to the leading strand slightly lower recombination levels for Beta without Exo and Gam were detected.

Thus, a deficiency in mismatch repair (MMR) eliminates sequence diversity effects. However, a deficiency in MMR, does not affect the lagging and leading strand bias. It is demonstrated herein that a reduction in the ability to perform mismatch repair can increase the frequency of homologous recombination by as much as 100-fold.

Example 5 ss-oligo Recombination with the $galK_{tyr145am}$ and galK< >cal-sacB Mutants: RecA Function Affects Recombination with a Large Heterology An ss oligo is capable of correcting either the $galK_{tyr145am}$ or galK< >cat-sacB. When the lagging strand oligo (Oligo 100) was used to correct the $galK_{tyr145am}$ of HME6, there were $3.5 \times 10^5$ recombinants per $10^8$ cells surviving the electroporation. This same oligo was also capable of removing a 3.3 kb cat-sacB heterology, from HME31 with nearly the same rate $-8.6 \times 10^4$ recombinants per $10^8$ survivors. The ability of a leading strand oligo (Oligo 101) to correct the same lesions was tested. The efficiency of recombination was reduced 10-fold for both HME6 and HME31.

Previous work had shown ssDNA recombination was independent of RecA function when the $galK_{tyr145am}$ point mutation was corrected with an ss oligo (Ellis, supra, 2001). A recA mutation was moved into HME31 to determine if there was an effect of RecA function on recombination with of a large heterology. A slight decrease of Gal+ colonies was found with lagging strand Oligo 100, but a 7-fold decrease in Gal+ recombinants was found when Oligo 101 (leading strand) is used.

No significant influence of transcription on strand bias was detected with the chromosomal gal operon, under conditions known to have a large effect on transcription levels. Without being bound by theory, it is believed that the mismatch repair system recognizes and repairs mismatches at the replication fork. Thus, as demonstrated herein MMR limits SSO-mediated recombination. Thus, in order to increase recombination frequency using recombineering technology, strains can be utilized that include one or more mutations in the MMR system, such as, but not to mutS, mutH, uvrD, dam, and/or mutL genes. These strains are disclosed herein, as are methods to maximize recombination frequency using SSO or double stranded DNA in these strains.

It will be apparent that the precise details of the methods or compositions described may be varied or modified without departing from the spirit of the described invention. We claim all such modifications and variations that fall within the scope and spirit of the claims below.

The invention claimed is:

1. A method for inducing homologous recombination in a bacterial host cell comprising a target nucleic acid, the method comprising:

introducing a single-stranded nucleic acid molecule or double-stranded nucleic acid molecule into the bacterial host cell, wherein the single-stranded nucleic acid molecule or double-stranded nucleic acid comprises a sufficient number of nucleotides homologous to the target nucleic acid to enable homologous recombination with the target nucleic acid, and wherein the bacterial host cell comprises a de-repressible promoter operably linked to a nucleic acid encoding a single-stranded binding protein wherein the bacterial host cell is deficient for the production of MutH, MutS, uvrD or MutL such that the bacterial host cell is deficient for mismatch repair, wherein the bacterial host cell is an *E. coli* host cell; and inducing expression of the single-stranded binding protein in the bacterial host cell;

thereby inducing homologous recombination of the single-stranded nucleic acid molecule or the double stranded nucleic acid molecule with the target nucleic acid in the bacterial host cell.

2. The method of claim 1, wherein the single-stranded nucleic acid molecule or double-stranded nucleic acid molecule comprises at least about 25 nucleotides homologous to the target nucleic acid.

3. The method of claim 1, wherein the single-stranded DNA binding polypeptide is lambda Beta or RecT.

4. The method of claim 3, wherein the single-stranded DNA binding polypeptide is Beta.

5. The method of claim 1, wherein the de-repressible promoter is the PL promoter.

6. The method of claim 1, wherein the bacterial host cell comprises a mutation in a nucleic acid encoding MutH, MutS or MutL, rending the bacterial host cell deficient for mismatch repair.

7. The method of claim 1, wherein the bacterial cell is deficient for the production of functional MutH polypeptide as compared to a wild-type *E. coli* cell.

8. The method of claim 1, wherein the bacterial host cell is deficient for the production of functional MutS polypeptide as compared to a wild-type *E. coil* cell.

9. The method of claim 1, wherein the bacterial host cell is deficient for the production of functional MutL polypeptide as compared to a wild-type *E. coil* cell.

10. The method of claim 1, wherein the bacterial host cell is deficient for the production of functional uvrD polypeptide as compared to a wild-type *E. coil* cell.

11. The method of claim 1, wherein single-stranded nucleic acid molecule or the double-stranded nucleic acid molecule comprises about 25 nucleotides to about 1,000 nucleotides homologous to the target nucleic acid sequence.

12. The method of claim 1, wherein a bacterial artificial chromosome comprises the target nucleic acid.

13. A method for inducing homologous recombination between a single-stranded nucleic acid molecule of at least 25 nucleotides in length and a target nucleic acid sequence in a bacterial host cell, the method comprising:

inducing the expression of a single-stranded binding protein in the bacterial host cell wherein the bacterial host cell comprises a de-repressible promoter operably linked to a nucleic acid encoding Beta or RecT and wherein the bacterial host cell comprises a mutation in a nucleic acid encoding MutH, MutS, uvrD or MutL, rendering the bacterial host cell deficient for mismatch repair, wherein the bacterial host cell is an *E. coil* host cell, thereby inducing homologous recombination of the single-stranded nucleic acid molecule with the target nucleic acid sequence in the bacterial host cell, wherein the nucleic acid sequence of the single-stranded nucleic acid molecule differs from a homologous section of the target nucleic acid sequence by about one nucleotide to about five nucleotides.

14. The method of claim 13, wherein the bacterial host cell comprises an extrachromosomal element comprising the target nucleic acid sequence.

15. The method of claim 13, wherein the nucleic acid sequence of the single-stranded nucleic acid molecule differs from a homologous section of the target nucleic acid sequence by one nucleotide.

16. The method of claim 13, wherein the nucleic acid sequence of the single-stranded nucleic acid molecule differs from a homologous section of the target nucleic acid sequence by about one to about three nucleotides.

17. The method of claim 13, wherein the single-stranded binding protein is Beta.

18. The method of claim 13, wherein the bacterial host cell is deficient for the production of functional MutL polypeptide as compared to a wild-type cell.

19. The method of claim 13, wherein the bacterial host cell is deficient for the production of functional MutS polypeptide as compared to a wild-type cell.

20. The method of claim 13, wherein the bacterial host cell is deficient for the production of functional MutH polypeptide as compared to a wild-type cell.

21. The method of claim 13, wherein the bacterial host cell is deficient for the production of functional uvrD polypeptide as compared to a wild-type cell.

22. The method of claim 13, wherein the bacterial cell is a DY380 cell, or an HME6 cell, or DY330 cell comprising a mutation in an nucleic acid encoding one or more of MutS, MutH, uvrD or MutL.

23. The method of claim 13, wherein the de-repressible promoter is PL.

24. A method for inserting a nucleic acid molecule into a target nucleic acid in a bacterial host cell, the method comprising:

introducing into the bacterial host cell a single-stranded nucleic acid of at least 25 nucleotides in length sufficiently homologous for recombination to occur with the target nucleic acid, but not identical to the target nucleic acid, wherein the bacterial host cell comprises a nucleic acid sequence encoding Beta operably linked to a de-repressible promoter, and wherein the bacterial cell has a mutation in a nucleic acid encoding MutS, MutH, uvrD or MutL such that mismatch repair is impaired in the bacterial host cell, and wherein the bacterial host cell is an *E. coli* host cell; and inducing expression of Beta from the de-repressible promoter, thereby inducing homologous recombination between the single-stranded DNA and the target nucleic acid, and thereby introducing the nucleic acid molecule into the target nucleic acid in the bacterial cell.

25. The method of claim 24, wherein the single-stranded nucleic acid is homologous to a lagging strand of the target nucleic acid.

26. The method of claim 24, wherein the single-stranded nucleic acid is homologous to a leading strand of the target nucleic acid.

27. The method of claim 24, wherein the target nucleic acid is a bacterial artificial chromosome (BAC), P1 artificial chromosome, or yeast artificial chromosome.

28. The method of claim 24, wherein the bacterial host cell comprises a nucleic acid encoding Exo or Gam.

29. The method of claim 24, wherein the bacterial host cell does not comprise a nucleic acid encoding Exo or Gam.

30. The method of claim 24, wherein the bacterial host cell comprises an extrachromosomal element comprising the target nucleic acid sequence.

31. The method of claim 24, wherein a chromosome of the cell comprises the target nucleic acid sequence.

32. A method of introducing a mutation into a target nucleic acid in a bacterial host cell, the method comprising:

introducing a first single-stranded nucleic acid of at least 30 nucleotides in length homologous to the target nucleic acid into the bacterial host cell; wherein the single-stranded nucleic acid is not identical to the target nucleic acid, and wherein the cell comprises a de-repressible promoter operably linked to a nucleic acid sequence encoding Beta, and wherein the bacterial host cell does not express functional uvrD, MutS, MutH, MutL polypeptide, or a combination thereof, and wherein the bacterial host cell is an *E. coli* host cell;

inducing the expression of Beta from the de-repressible promoter, thereby inducing recombination of the single-stranded nucleic acid with the target nucleic acid in the cell, wherein the recombination of the single-stranded nucleic acid with the target nucleic acid introduces the mutation into the target nucleic acid.

33. The method of claim 32, wherein the single-stranded nucleic acid is homologous to a lagging strand of the target nucleic acid.

34. The method of claim 32, wherein the first single-stranded nucleic acid is homologous to a leading strand of the target nucleic acid.

35. The method of claim 32, wherein the mutation is a deletion.

36. The method of claim 32, wherein the mutation is a point mutation.

37. The method of claim 32, wherein the mutation is an insertion.

* * * * *

```
                        SEQUENCE LISTING

<160> NUMBER OF SEQ ID NOS: 24

<210> SEQ ID NO 1
<211> LENGTH: 12
<212> TYPE: DNA
<213> ORGANISM: Artificial sequence
<220> FEATURE:
<223> OTHER INFORMATION: primer

<400> SEQUENCE: 1 aggggggcaag ta                                                        12

<210> SEQ ID NO 2
<211> LENGTH: 12
<212> TYPE: DNA
<213> ORGANISM: Artificial sequence
<220> FEATURE:
<223> OTHER INFORMATION: primer

<400> SEQUENCE: 2
ttctcaagga ga                                                         12

<210> SEQ ID NO 3
<211> LENGTH: 12
<212> TYPE: DNA
<213> ORGANISM: Artificial sequence
<220> FEATURE:
<223> OTHER INFORMATION: primer

<400> SEQUENCE: 3
aggtatcatg ac                                                         12

<210> SEQ ID NO 4
<211> LENGTH: 12
<212> TYPE: DNA
<213> ORGANISM: Artificial sequence
<220> FEATURE:
<223> OTHER INFORMATION: primer

<400> SEQUENCE: 4
agtgcactac tg                                                         12

<210> SEQ ID NO 5
<211> LENGTH: 12
<212> TYPE: DNA
<213> ORGANISM: Artificial sequence
<220> FEATURE:
<223> OTHER INFORMATION: primer

<400> SEQUENCE: 5
```

```
caactggcga ac                                                    12

<210> SEQ ID NO 6
<211> LENGTH: 12
<212> TYPE: DNA
<213> ORGANISM: Artificial sequence
<220> FEATURE:
<223> OTHER INFORMATION: primer

<400> SEQUENCE: 6
tacatccggc ga                                                    12

<210> SEQ ID NO 7
<211> LENGTH: 12
<212> TYPE: DNA
<213> ORGANISM: Artificial sequence
<220> FEATURE:
<223> OTHER INFORMATION: primer

<400> SEQUENCE: 7
ggacataacc cc                                                    12

<210> SEQ ID NO 8
<211> LENGTH: 12
<212> TYPE: DNA
<213> ORGANISM: Artificial sequence
<220> FEATURE:
<223> OTHER INFORMATION: primer

<400> SEQUENCE: 8
taataacaat tc                                                    12

<210> SEQ ID NO 9
<211> LENGTH: 12
<212> TYPE: DNA
<213> ORGANISM: Artificial sequence
<220> FEATURE:
<223> OTHER INFORMATION: primer

<400> SEQUENCE: 9
ggacgtttct ta                                                    12

<210> SEQ ID NO 10
<211> LENGTH: 12
<212> TYPE: DNA
<213> ORGANISM: Artificial sequence
<220> FEATURE:
<223> OTHER INFORMATION: primer

<400> SEQUENCE: 10
taacgttgcc gg                                                    12

<210> SEQ ID NO 11
<211> LENGTH: 70
<212> TYPE: DNA
<213> ORGANISM: Artificial sequence
<220> FEATURE:
<223> OTHER INFORMATION: primer

<400> SEQUENCE: 11
aagtcgcggt cggaaccgta ttgcagcagc tttatcatct gccgctggac ggcgcacaaa    60
tcgcgcttaa                                                           70

<210> SEQ ID NO 12
<211> LENGTH: 44
```

```
<212> TYPE: DNA
<213> ORGANISM: Artificial sequence
<220> FEATURE:
<223> OTHER INFORMATION: primer

<400> SEQUENCE: 12
ggttctccgg ccgcttgggt ggagaggcta ttcggctagg actg                       44

<210> SEQ ID NO 13
<211> LENGTH: 20
<212> TYPE: DNA
<213> ORGANISM: Artificial sequence
<220> FEATURE:
<223> OTHER INFORMATION: primer

<400> SEQUENCE: 13
tattcggcaa gcaggcatcg                                                  20

<210> SEQ ID NO 14
<211> LENGTH: 65
<212> TYPE: DNA
<213> ORGANISM: Artificial sequence
<220> FEATURE:
<223> OTHER INFORMATION: primer

<400> SEQUENCE: 14
ggcgctgcaa aaattctttg tcgaacaggg tgtctggatc taatgcgccg ctacagggcg      60
cgtaa                                                                  65

<210> SEQ ID NO 15
<211> LENGTH: 65
<212> TYPE: DNA
<213> ORGANISM: Artificial sequence
<220> FEATURE:
<223> OTHER INFORMATION: primer

<400> SEQUENCE: 15
ggcgctgcaa aaattctttg tcgaacaggg tgtctggatc taatgcgccg ctacagggcg      60
cgtaa                                                                  65

<210> SEQ ID NO 16
<211> LENGTH: 24
<212> TYPE: DNA
<213> ORGANISM: Artificial sequence
<220> FEATURE:
<223> OTHER INFORMATION: primer

<400> SEQUENCE: 16
acgttaaatc tatcaccgca aggg                                             24

<210> SEQ ID NO 17
<211> LENGTH: 20
<212> TYPE: DNA
<213> ORGANISM: Artificial sequence
<220> FEATURE:
<223> OTHER INFORMATION: primer

<400> SEQUENCE: 17
tattcggcaa gcaggcatcg                                                  20

<210> SEQ ID NO 18
<211> LENGTH: 15
<212> TYPE: DNA
<213> ORGANISM: Artificial sequence
<220> FEATURE:
```

```
<223> OTHER INFORMATION: primer

<400> SEQUENCE: 18
cagctttatc atctg                                                    15

<210> SEQ ID NO 19
<211> LENGTH: 15
<212> TYPE: DNA
<213> ORGANISM: Artificial sequence
<220> FEATURE:
<223> OTHER INFORMATION: primer

<400> SEQUENCE: 19
cagctttacc atctg                                                    15

<210> SEQ ID NO 20
<211> LENGTH: 15
<212> TYPE: DNA
<213> ORGANISM: Artificial sequence
<220> FEATURE:
<223> OTHER INFORMATION: primer

<400> SEQUENCE: 20
cagctttagc atctg                                                    15

<210> SEQ ID NO 21
<211> LENGTH: 15
<212> TYPE: DNA
<213> ORGANISM: Artificial sequence
<220> FEATURE:
<223> OTHER INFORMATION: primer

<400> SEQUENCE: 21
cagatgctaa agctg                                                    15

<210> SEQ ID NO 22
<211> LENGTH: 15
<212> TYPE: DNA
<213> ORGANISM: Artificial sequence
<220> FEATURE:
<223> OTHER INFORMATION: primer

<400> SEQUENCE: 22
cagatgataa agctg                                                    15

<210> SEQ ID NO 23
<211> LENGTH: 15
<212> TYPE: DNA
<213> ORGANISM: Artificial sequence
<220> FEATURE:
<223> OTHER INFORMATION: primer

<400> SEQUENCE: 23
cagatggtaa agctg                                                    15

<210> SEQ ID NO 24
<211> LENGTH: 10
<212> TYPE: DNA
<213> ORGANISM: Artificial sequence
<220> FEATURE:
<223> OTHER INFORMATION: example sequence

<400> SEQUENCE: 24
cccccggggg                                                          10
```